United States Patent [19]

Trokel

[11] Patent Number: 5,108,388
[45] Date of Patent: Apr. 28, 1992

[54] LASER SURGERY METHOD
[75] Inventor: Stephen L. Trokel, New York, N.Y.
[73] Assignee: Visx, Incorporated, Sunnyvale, Calif.
[21] Appl. No.: 109,812
[22] Filed: Oct. 16, 1987

Related U.S. Application Data

[63] Continuation of Ser. No. 859,212, May 2, 1986, abandoned, which is a continuation of Ser. No. 561,804, Dec. 15, 1983, abandoned.

[51] Int. Cl.$^5$ ................................................ A61N 5/06
[52] U.S. Cl. ........................................ 606/5; 606/13; 606/3; 128/395
[58] Field of Search ............... 128/303.1, 395; 606/5, 606/3, 13

[56] References Cited

U.S. PATENT DOCUMENTS

| | | | |
|---|---|---|---|
| 3,710,798 | 1/1973 | Bredemeier | 128/395 |
| 3,769,963 | 11/1973 | Goldman et al. | 128/303.1 |
| 4,170,997 | 10/1979 | Pinnow et al. | 433/114 |
| 4,258,334 | 3/1981 | McCusker et al. | |
| 4,266,548 | 5/1981 | Davi | 128/303.1 |
| 4,309,998 | 1/1982 | Aron nee Rosa et al. | 128/303.1 |
| 4,326,529 | 4/1982 | Doss et al. | |
| 4,331,937 | 5/1982 | Brown et al. | |
| 4,381,007 | 4/1983 | Doss | |
| 4,409,979 | 10/1983 | Roussel et al. | 128/395 |
| 4,461,294 | 7/1984 | Baron | 128/303.1 |
| 4,665,913 | 5/1987 | L'Esperance | 128/303.1 |
| 4,729,372 | 3/1988 | L'Esperance | 606/5 |
| 4,732,148 | 3/1988 | L'Esperance | 606/5 |
| 4,769,963 | 9/1988 | Goldman et al. | 128/303.1 |

FOREIGN PATENT DOCUMENTS 111060 6/1984 European Pat. Off. ......... 128/303.1

OTHER PUBLICATIONS

"Response of the Corneal Epithelium to KrF Excimer Laser Pulses", J. Taboada et al., Health Physics, vol. 40, May 1981, pp. 677–683.

"Far UV Photoetching of Organic Material" Srinwasan et al., Laser Focus, May 1983.

"Excimer Laser Surgery of the Cornea" by Stephen Trokel et al., pp. 710–715, American Journal of Ophthalmology, vol. 96, No. 6, December 1983.

"An Extreme Sensitivity in the Corneal Epithelium To Far UV ArF Excimer Laser Pulses" by Taboada et al., Proc. of the Scientific Program Aerospace Medial Association, 1981 meeting pp. 98–99.

*Primary Examiner*—David M. Shay
*Attorney, Agent, or Firm*—Oblon, Spivak, McClelland, Maier & Neustadt

[57] ABSTRACT

An argon-flouride excimer laser or other laser source capable of generating far-ultraviolet radiation at 193 nm is pulsed with energy densities of greater than 20 mj per cm$^2$ at a repetition rate up to 25 pulses per second to direct its radiation through a mask and onto corneal tissue, or other biological matter, to form a groove therein of predetermined configuration and depth by a process of ablative photodecomposition. The masks are formed with a slit, circular, crescent or other openings of widths between 30 and 800 microns, and may even be formed to provide a graded intensity center to edge. The mask is reflective or composed of or faced with an organic polymer to prevent heat build-up. Each micron of the depth of a 200 micron deep groove formed in corneal tissue, for example, resulted from the application of 1 joule per square centimeter of radiation, from a series of pulses delivered at intensities of between 100 mj and 200 mj per square centimeter and at a laser pulse rate of between 1 and 25 Hertz; the entire groove taking 100 seconds.

5 Claims, 3 Drawing Sheets

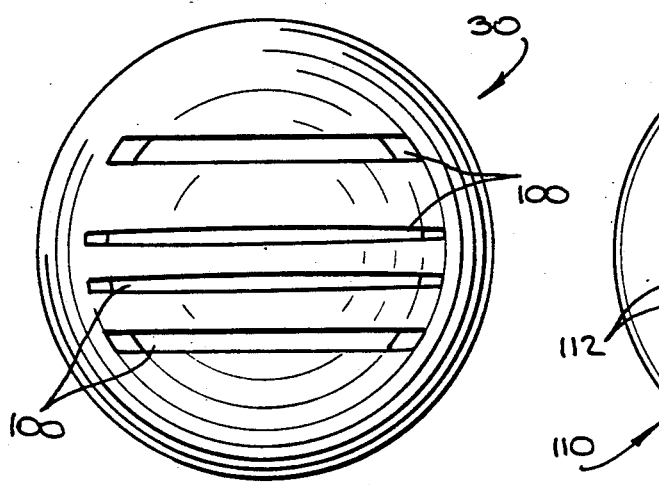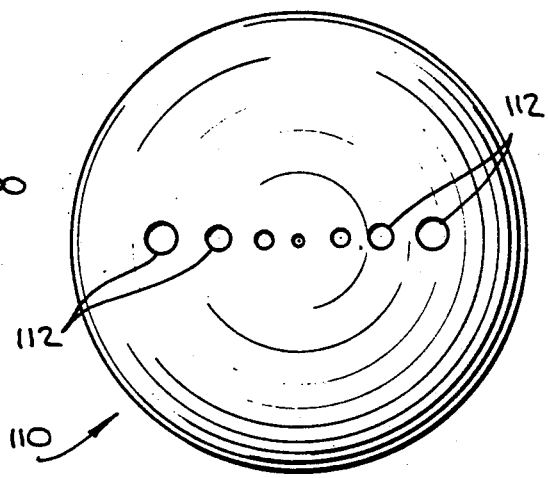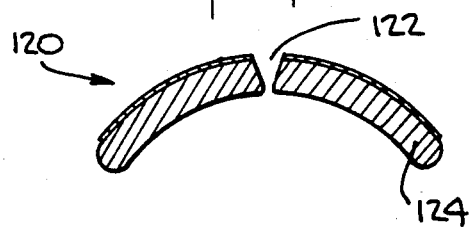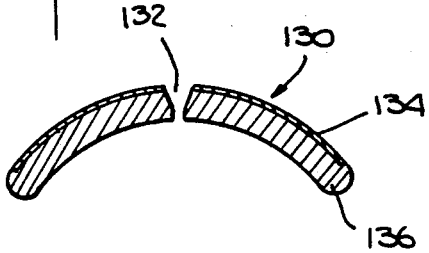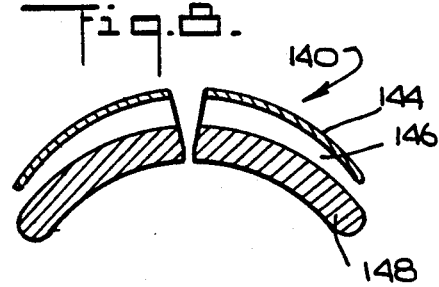

LASER SURGERY METHOD

This is a continuation of co-pending application Ser. No. 859,212, filed on May 2, 1986, abandoned, which in turn is a continuation of application Ser. No. 561,804, filed on Dec. 15, 1983, abandonded.

BACKGROUND OF THE INVENTION

1. Field of Application

This invention relates to surgical apparatus and methods; and more particularly to laser source surgical apparatus and methods.

2. Description of the Prior Art

Surgical procedures, especially surgical procedres wherein animal or human biological tissue, or other matter, are to be removed from a predetermined area and to a predetermined depth, require great surgical skill. In such procedures the skill of the surgeon is often enhanced by the use of apparatus particularly designed for surgical purposes. Such apparatus is more often than not very expensive, and in many instances requires complex procedures and a highly skilled or trained operator. But, regardles of the expense of the apparatus, complexity of the procedure or skill or training required to use the apparatus; it is often the availability of the apparatus that makes a particular surgical procedure possible. However, quite often the apparatus, and associated surgical method, while facilitating a particular surgical procedure, produce unwanted effects on or to areas of the human or animal adjacent to those requiring the surgery.

Laser source apparatus has been utilized for surgical procedures; especially in ophthalmology. In such apparatus a collimated beam of light, generated or produced by the laser sources, is directed so as to focus on the area to be operated on. The light energy produced by the laser is converted to heat energy which, in turn, is utilized for the surgery. Such laser source facilitated surgical procedures are sometimes and may be otherwise referred to as thermal photocoagulation as a fine controlled burn is produced. Other laser systems focus high powered pulses of light of sufficient intensity to produce optical (or dielectric) breakdown. This produces a surgical effect referred to as photodisruption because the tissues are "disrupted" by the pulsar burn and associated shock wave.

Some available laser source apparatus for those surgical purposes, and associated surgical procedures, are described: in U.S. Pat. No. 3,982,541 granted on Sep. 28, 1976 to F. A. L'Esperance, Jr., for Eye Surgical Instrument; in U.S. Pat. No. 4,309,998 granted on Jan. 12, 1982 to D. S. Aron nee Rose et al for Process And Apparatus For Ophthalmic Surgery; in U.S. Pat. No. 4,336,809 granted on Jun. 29, 1982 to W. G. Clark for Human And Animal Tissue Photoradiation System And Method; and in U.S. Pat. No. 4,391,275 granted on Jul. 5, 1983 to F. Frankhauser, et al for Method For The Surgical Treatment Of The Eye.

However, utilization of such apparatus more often than desired effects unwanted changes in adjacent remaining structures, thermal damage to areas adjacent that requiring the surgical procedure, and undesirable irregular edges of the interation site produced by the forces of optical breakdown. In addition, not every laser is suitable or acceptable if the surgeon is seeking the best possible results from the surgical procedures. A new tissue interaction has been observed using pulsed ultravoilet light. A direct photochemical effect is observed which interacts exclusively with the irradiated tissues and produces no discernible effect upon the adjacent, unirradiated tissues. For lasers generating ultraviolet wavelengths shorter than 193 nm (nanometers) it has been found that optical delivery systems become extremely difficult to build because of the limited availability of refracting material; while for lasers generating wavelengths longer than 200 nm thermal effects become more dominant and the percentage of true ablative photodecomposition lessens.

Surgical procedures may be performed using pulsed ultraviolet light utilizing a mix of complete photoablation with some thermal effect as desired by the operating surgeon.

SUMMARY OF THE INVENTION

It is therefore an object of this invention to provide a new and improved laser source surgical apparatus.

It is another object of this invention to provide a new and improved method of laser surgery.

It is yet another object of this invention to provide a new and improved laser source apparatus for producing ablative photo-decomposition in ophthalmic surgery.

It is still another object of this invention to provide a new and improved method for surgery utilizing far-ultraviolet laser source which produces ablative photo-decomposition.

It is yet still another object of this invention to provide a new and improved laser source apparatus for ophthalmological surgery.

It is yet still another object of this invention to provide a new and improved method for laser source ophthalmological surgery.

It is a further object of this invention to provide a new and improved surgical apparatus utilizing a far-ultraviolet laser.

It is still a further object of this invention to provide a new and improved surgical method utilizing a far-ultraviolet argon-fluoride excimer laser.

This invention involves surgical apparatus and methods utilizing laser generated light at particular wavelengths to effect ablative photodecomposition of particular areas of animal or human biological matter to a particular depth; and comtemplates utilizing a laser producing far-ultraviolet radiation at a wavelength of 193 nm (nanometers) and directing same to the particular area through a mask of predetermined configuration and intensity, and in pulses of predetermined intensity for predetermined time periods so as to produce an opening of sharply defined edges and depth.

Other objects, features and advantages of the invention in its details of construction and arrangement of parts will be seen from the above, from the following description of the preferred embodiment when considered with the drawing and from the appended claims.

BRIEF DESCRIPTION OF THE DRAWING

In the drawing:

FIG. 4 is a plan view of a mask usable with the apparatus and system of FIG. 1;

FIG. 5 is a plan view of another mask usable with the apparatus and system of FIG. 1;

FIG. 6 is a sectional view through a mask usable with the apparatus and system of FIG. 1;

FIG. 7 is a sectional view of another mask usable with the apparatus and system of FIG. 1;

FIG. 8 is a sectional view of yet another mask usable with the apparatus and system of FIG. 1;

DESCRIPTION OF THE PREFERRED EMBODIMENT

For convenience, the invention will be described as applied to a laser photoablation and method utilizing an argon-fluoride excimer laser which generates far-ultraviolet radiation at 193 nm (nanometers) at predetermined pulse energy densities and repetitio rates. Far-ultraviolet light may be produced by other lasers to be incorporated into this ophthalmic surgical system. Furthermore, the wavelengths of light applicable extend to 248 nm in spite of the less pure photodecomposition noted. The laser beam is thereafter directed through a mask formed from particular material and with either one or more slit or circular openings to impinge upon an area of the cornea of an eye to form therein a groove of predetermined peripheral configuration and depth. It should be understood, nevertheless, that without departing from the invention: that the mask openings can be of any convenient peripheral configuration; that the masks may be formed of any appropriate material; that a fiber optic pipe and rod delivery system may be utilized without masks and that the apparatus and system may be utilized for procedures on other tissues and biological matter such as dental caries, human skin and the like.

Figure 1:
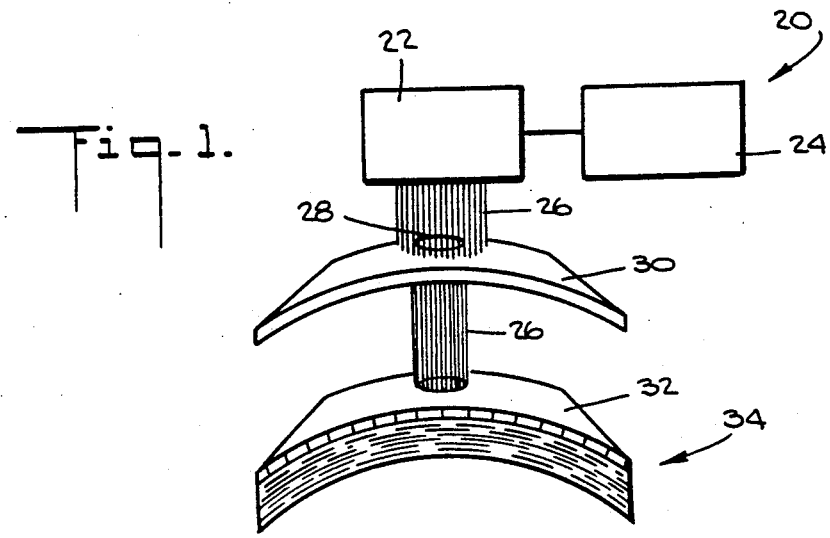
FIG. 1 is a schematic illustration of a photoablation apparatus and system incorporating the instant invention.

With reference to FIG. 1, there is generally shown at 20 a photoablation laser surgery apparatus and system utilizing a laser delivery system 22 and associated power supply and control system 24 by which a laser beam 26 is directed through openings 28 formed in a mask 30 and onto the cornea 32 of an eye 34, of either a human or an animal.

Laser delivery system 22 includes an argon-fluoride excimer laser such as one currently manufactured by Lamda Physik as their Model 201E. However, it is understood that other laser sources may be used to produce the effective ultraviolet light. Laser system 22 generates a laser beam 26 in the far-ultraviolet range of 193 nm (nanometers). Other ranges of ultraviolet wave lengths may be chosen. Power supply and control 24 is conventionally available and is interconnected to laser system 22 so that the output thereof is pulses at pulse energy densities of greater than 420 mj per $cm^2$ (milijoules per centimeter square) at a repetition rate up to 25 pulses per second.

Figure 2:
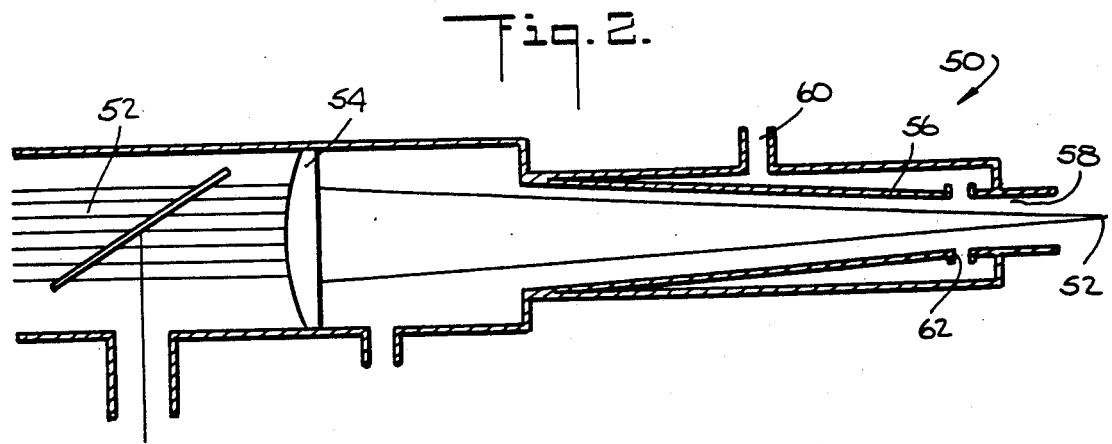
FIG. 2 is a schematic illustration of a laser delivery system for use with the apparatus and system of FIG. 1.

FIG. 2 illustrates a laser delivery system 50 wherein an ultra-violet laser beam 52 is directed through lens 54 and then through a passage 56 and opening 58. An appropriate opening 60 is provided to passage 56 for infusion of Nitrogen or other similar gases; while another opening 62 is provided for passage 56 to provide a high vacuum therefor.

Figure 3:
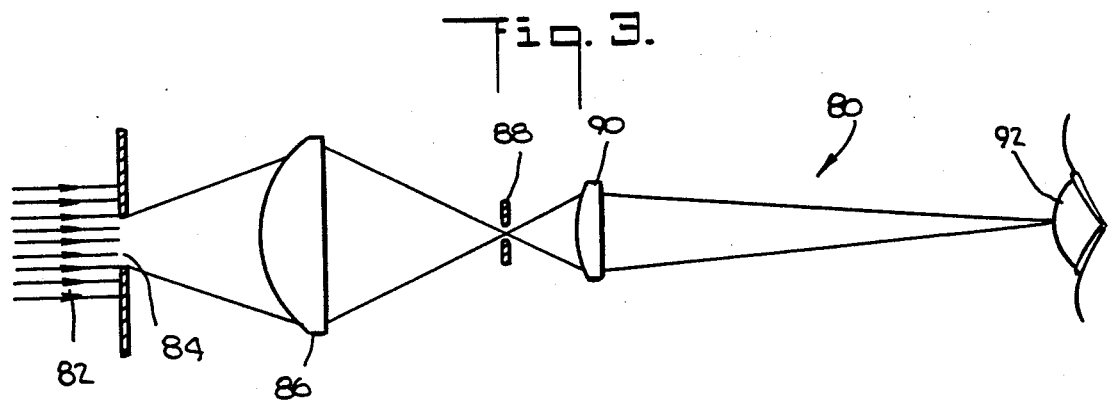
FIG. 3 is a schematic illustration of an opthalmic delivery system for use with the apparatus and system of FIG. 1.

In FIG. 3 there is shown an ophthalmic delivery system 80 for generatiang and delivering a laser generated ultra-violet laser beam 82 through a variable slit 84 to and through a lens 86, an aperture 88 another lens 90 and onto an area, such as an eye 92, upon which a surgical procedure is to be performed.

Mask 30 (FIGS. 1 and 4) is formed from aluminum, or other appropriate material, and includes a number of slits 100 formed therethrough, and ranging in width from 150 to 800 microns. While four slits have been shown for mask 30 it should be understood that a lesser or greater number of slits can be provided for mask 30, and that the widths as well as the slit configuration appropriately selected. An alternate mask 110, shown in FIG. 5, is formed with seven holes 112 drilled or otherwise formed therethrough. Holes 112 range in diameter from 100 microns to 750 microns. It should be understood that openings of any desired configuration (crescents, concentric rings, etc.) may be formed through masks 30 and 110; and that in addition, the mask may also be formed to provide a graded intensity center to edge or edge to center. The mask may be clad or covered with plastic or other polymers to prevent heating of the mask. The organic material will prevent ultra-violet light from striking the mask and heating it directly. The cladding prevents heating by being ablated by the ultra-violet light which is being shielded from the eye.

In FIG. 6 there is shown a mask 120 with an opening 122 and having a surface of 2000°A chrome formed onto a base 124 of polymetal methacrylate to reflect the ultra-violet light and prevent heating; and which is stablized by vacuum seal.

In FIG. 7, there is a mask 130 with an opening 132.

FIG. 8 shows still another alternate mask 140 with an opening 142. Mask 140 includes one or more metal cooling vanes 144 separated by an air space 146 from, but otherwise carried by or supported with respect to, a base 148 of stainless steel; all stabilized by a vacuum seal.

While masks 120, 130, and 140 have been shown with single openings 122, 132, 142 respectively it should be understood that any suitable number of openings may be formed in the masks, and that such openings may be formed to any appropriate configuration and width.

In use laser apparatus 20 is positioned with respect to the area of tissue, biological matter, or the like upon which the surgical procedure is to be performed. In this instance laser 20 is disposed with respect to cornea 32 of an eye 34 so that laser beam 26 will be directed towards mask 30 and then upon cornea 32. The output of laser 20 is delivered in a series of pulses under control of laser delivery system 22 and laser power supply and control system 24. For each micron depth of corneal tissue to be ablated one joule per square centimeter was applied. Thus in forming a 200 micron deep groove, for example, 200 joules per $cm^2$ would be required. This was delivered in a series of pulses varying in intensity between 100 and 200 mj per square centimeter depending upon the area of the final focus of laser apparatus 20.

The laser pulse rate for apparatus 20 was between 1 and 25 Hertz; and the pulses were delivered until sufficient total energy achieved the desired depth of cut. The maximum exposure time for the complete section of the cornea as described required 100 seconds (700 mj per cm$^2$). More rapid pulse rates create tissue heating distortion from gas pressure backup in the irradiated area. Higher energy densities in the irradiated area produce unwanted shock effects.

Figure 9:
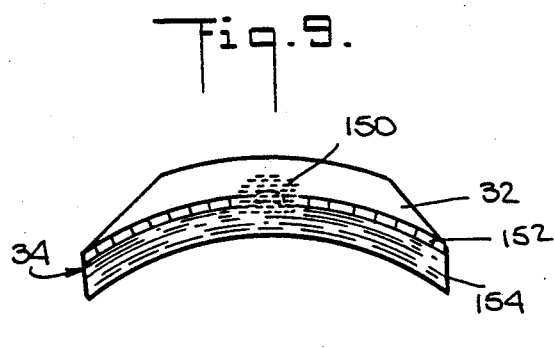
FIG. 9 is a sectional view through the schematic eye of FIG. 1 during the surgical procedure according to the instant invention.
Figure 10:
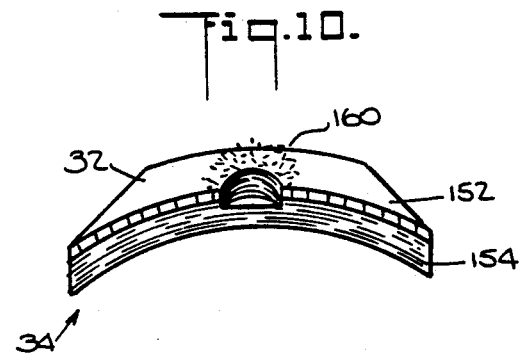
FIG. 10 is a sectional view through the schematic eye of FIGS. 1 and 9 following the surgical procedure according to the instant invention.

In FIG. 9 eye 34 is shown during the above described procedure and illustrating the bond breaking occurring at 150 in the epthelium 152 and stromal collagen 154; while in FIG. 10 the ablated groove 160 is shown.

Figure 11:
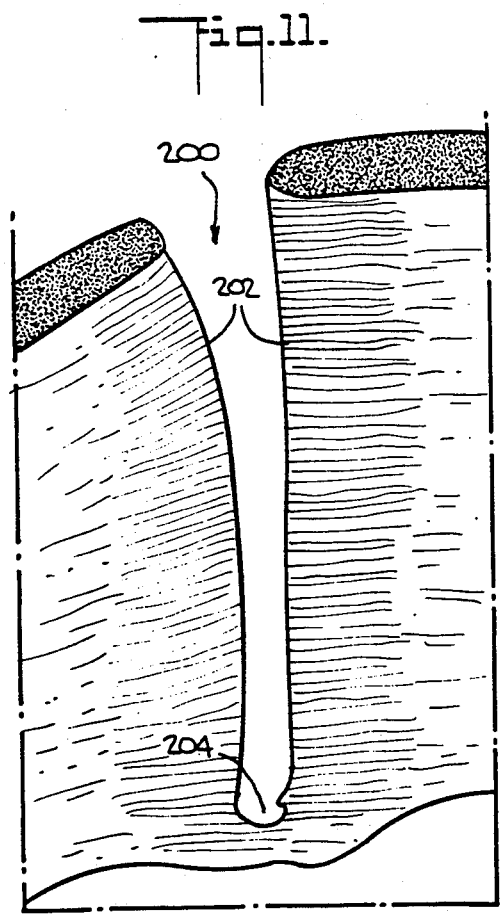
FIG. 11 is a sectional view perpendicular to a groove formed by photoablation according to the instant invention using the mask of FIG. 4.

It should be noted that by utilizing apparatus 20 and the described procedure a groove 200 (FIG. 11) can be formed with parallel walls 202 and a square bottom 204.

Figure 12:
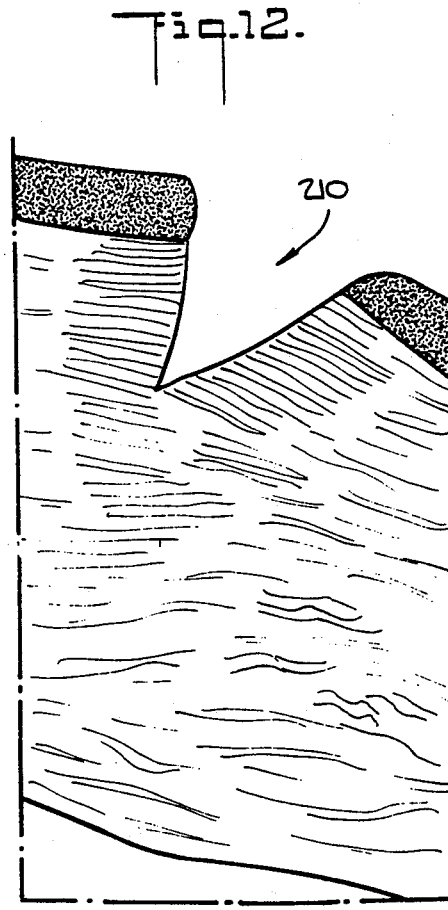
FIG. 12 is a schematic view perpendicular to a V-shaped groove formed by photoablation according to the instant invention.

Alternatively, a V-shaped groove 210 (FIG. 12) may be formed by apparatus 20 and the described procedure by directing laser beam 28 so that it strikes cornea 32 obliquely. By doing so the energy distribution across a slit or other opening formed through mask 30 will cause the tissue to ablate more rapidly at one edge.

The described apparatus 20 and method causes a specific photo-chemical reaction and results in the ablation of corneal or other tissues without thermal damage to the adjacent remaining structures. The method allows incisions of controlled depth and shape. Defined volumes of tissue can be removed by masking to control the area ablating the tissue to a predetermined depth.

The corneal epithelium, for example, shows an extreme sensitivity to the 193 nm light emitted by the argon-flouride excimer laser of apparatus 20. The resulting ablative photo-decomposition of the tissue are broken into smaller volatile fragments by the direct photo-chemical interaction without heating the remaining adjacent tissues. Ultraviolet light at 193 nm is highly energetic, each photon having 6.4 electron volts. The high energy of each photon provides the photo-chemical energy of the described apparatus and method directly breaks intramolecular bonds.

Laser systems generating wavelengths larger than 193 nm thermally vaporize tissues with changes in adjacent remaining structures; while laser systems generating wavelengths shorter than 193 nm are difficult to build because of the limited availability of refracting material. Tissues sectioned with a frequency doubled YAG laser run in a thermal mode show irregular edges of the interaction site produced by high tissue temperatures.

Apparatus 20 and the described method will produce an incision resembling that formed by a surgical cut. There will be a parallel between the gross corneal appearance and the mask, and no distortion of the stromal lamellae or epithelial edge. The groove walls will be parallel along their entire lenght and have a squared bottom.

The ablative photodecomposition accomplished by the described apparatus and method will provide grooves of a precisely determined shape and to a precisely determined depth. This has the same clinical indication as lamellar keratectomy as precise excision of the corneal tissue can be accomplished. In addition, a controlled penetrating corneal incision can, in principal, be done for corneal transplantation.

Radial incisions as well as concentric rings and crescents can be accomplished with the described apparatus and method. In fact, the laser light of the described method and apparatus can be applied to a circular mask of graded intensity center to edge. This would take away more tissue either centrally or peripherally depending on the distribution of light. The net effect would be either to steepen or flatten the cornea. The ability to make controlled radial incisions, or to selectively shape the cornea surface, allows modification of the refractive status of the eye.

As a further modification, apparatus 20 can be provided with a fiber optic pipe or rod delivery system to allow placement of UV laser light to intraocular structures. This would allow (a) controlled filtering filtering operation for glaucoma to be done subconjunctivally or via the anterior chamber; (b) A "phakoemulsification" could be done with pulsed ultraviolet light rather than a vibrating titanium rod; (c) the Fibroptic rod delivery systems allows placement of the unit in the eye to section vitreous membranes as an alternative to rotating or oscillating knives.

Additionally, such biber optic rod delivery system can be used in the treatment of dental caries by directing the light to the affected area or can be used in the removal of skin lesions.

As various possible embodiments might be made of the above invention, and as various changes might be made in the embodiments above set forth, it is to be understood that all matter herein described or shown in the accompanying drawings is to be interpreted as illustrative and not in a limiting sense. Thus, it will be understood by those skilled in the art that although preferred and alternative embodiments have been shown and described in accordance with the Patent Statutes, the invention is not limited thereto or thereby, since the embodiments of the invention particularly disclosed and described herein above are presented merely as an example of the invention. Other embodiments, forms, and modifications of the invention, coming within the proper scope and spirit of the appended claims, will of course readily suggest themselves to those skilled in the art. Thus, while there has been described what is at present considered to be the preferred embodiments of this invention, it will thus be obvious to those skilled in the art that various changes and modifications may be made therein, without departing from the invention, and it is, therefore, aimed in the apppended claims to cover all such changes and modifications as fall within the true spirit and scope of the invention, and it is understood that, although I have shown the preferred form of my invention, that various modifcations may be made in the details thereof, without departing from the spirit as comprehended by the following claims.

What is claimed is:

1. A method for producing a surgical excision of controlled depth and shape in a cornea by ablative photochemical decomposition of corneal tissue without thermal damage to the corneal tissue, said method comprising the steps of:

(a) generating a laser beam in the far ultraviolet region of the energy spectrum and at a wavelength selected to produce ablative photochemical decomposition of corneal tissue without thermal damage to the corneal tissue and (b) directing said radiation in a controlled manner onto said corneal tissue to induce ablative photochemical decomposition thereof in a volumetric removal of said corneal tissue without thermal heating to create a surgical excision of controlled depth and shape with depth penetration into the stroma.

2. The method of claim 1 wherein said selected wavelength is 193 nanometers.

3. A method for producing a surgical excision of controlled depth and shape in a cornea by ablative photochemical decomposition of corneal tissue without thermal damage to the corneal tissue, said method comprising the steps of:
   (a) generating a laser beam at a wavelength of 193 nanometers;
   (b) directing said laser beam onto a predetermined area of corneal tissue; and
   (c) controlling said laser beam so as to induce ablative photochemical decomposition of said corneal tissue in a volumetric removal of said corneal tissue without thermal damage to said corneal tissue to create a surgical excision of controlled depth and shape with depth penetration into the stroma.

4. The method of changing optical properties of an eye by operating solely upon the anterior surface of the cornea of the eye, which method comprises selective ultraviolet irradiation and attendant ablative photodecomposition of the anterior surface of the cornea in a volumetric removal of corneal tissue and with depth penetration into the stroma and to a predetermined curvature profile.

5. The method of using an ultraviolet laser to change the optical properties of an eye, which method comprises adjusting the intensity of laser beam projection to a level at which laser beam projection onto the anterior surface of the cornea of the eye will result in corneal-tissue ablation per unit time which is but a fraction of a predetermined maximum ablation depth into the stroma of the cornea, and directing the laser beam at the anterior surface of the cornea in a controlled manner to create at least one excision in the anterior surface of the cornea relative to the optic axis thereof by volumetric removal of corneal tissue in the course of ablative photodecomposition of the stroma causing a redefinition of the anterior surface of the cornea.

* * * * *

UNITED STATES PATENT AND TRADEMARK OFFICE
CERTIFICATE OF CORRECTION

PATENT NO. : 5,108,388

DATED : April 28, 1992

INVENTOR(S) : STEPHEN L. TROKEL

It is certified that error appears in the above-identified patent and that said Letters Patent is hereby corrected as shown below:

In column 1, line 15, delete "procedres" and insert --procedures--;

In column 1, line 24, delete "regardles" and insert --regardless--;

In column 1, line 34, delete ";" and insert --,--;

In column 1, line 64, delete "interation" and insert --interaction--;

In column 1, line 67, delete ".A" and insert new paragraph --A new tissue ...--

In column 2, line 1, delete "ultravoilet" and insert --ultraviolet--;

In column 2, line 5, insert "," after (nanometers);

In column 2, line 24, delete "photo-decomposition" and insert --photodecomposition--;

In column 2, line 26, delete "utilizing far-" and insert --utilizing a far- --;

In column 2, line 50, delete "and intensity";

In column 2, line 57, delete "drawing and" and insert --drawings, and--;

In column 2, line 58, delete "DRAWING" and insert --DRAWINGS--;

In column 2, line 60, delete "the drawing:" and insert -- the drawings:--;

In column 3, line 30, delete "repetitio" and insert --repetition--;

UNITED STATES PATENT AND TRADEMARK OFFICE
CERTIFICATE OF CORRECTION

PATENT NO. : 5,108,388

DATED : APRIL 28, 1992

INVENTOR(S) : STEPHEN L. TROKEL

It is certified that error appears in the above-identified patent and that said Letters Patent is hereby corrected as shown below:

In column 3, line 36, delete "either";

In column 3, line 40, delete "nevertheless, that" and insert -- nevertheless, that,--;

In column 3, line 41, delete "invention:" and insert --invention--;

In column 3, line 45, delete "masks and that" and insert --masks; and the--;

In column 3, line 65, delete "is pulses at" insert --is pulsed at--;

In column 4, line 27, delete "110; and that in" and insert --110 and that, in--

In column 4, line 39, delete "of polymetal" and insert --of polymethyl--;

In column 4, line 54, delete "use laser" and insert --use, laser--;

In column 5, line 12, delete "epthelium" and insert --epithelium--;

In column 5, line 32, delete "20. The result-" and insert --20. During the result- --;

Col. 5, line 33, delete "photo-decomposition" should read --photodecomposition -- and delete "tissue are" and insert --tissue is--;

Col. 5, line 34, delete "by the direct" and insert --by direct--

UNITED STATES PATENT AND TRADEMARK OFFICE
CERTIFICATE OF CORRECTION

PATENT NO. : 5,108,388

DATED : April 28, 1992

INVENTOR(S) : STEPHEN L. TROKEL

It is certified that error appears in the above-identified patent and that said Letters Patent is hereby corrected as shown below:

In column 5, lines 38-40, delete "each photon provides the photo-chemical energy of the described apparatus and method directly breaks intramolecular' and insert --each photon breaks intramolecular--;

In column 5, line 55, delete "lenght" and insert --length--;

In column 5, line 61, delete "keratectomy as" and insert --keratectomy, as--;

In column 6, line 11, delete "controlled filtering filtering" and insert --controlled filtering--;

In column 6, line 13, delete "(b) A" and insert --(b) a--;

In column 6, line 14, delete, "could be done" and insert --to be done--;

In column 6, line 15 & 16, delete, "rod; (c) the Fibroptic rod delivery systems allows placement of the unit" and insert --rod; and (c) placement of the unit--;

In column 6, line 19, delete, "such biber" and insert --such fiber--;

In column 6, line 34, delete, "herein above" and insert --hereinabove--;

In column 6, line 41, delete, "it will thus be" and insert --it will be obvious--;

UNITED STATES PATENT AND TRADEMARK OFFICE
CERTIFICATE OF CORRECTION

PATENT NO. : 5,108,388

DATED : April 28, 1992

INVENTOR(S) : STEPHEN L. TROKEL

It is certified that error appears in the above-identified patent and that said Letters Patent is hereby corrected as shown below:

In column 6, line 44, delete "apppended" and insert --appended--;

In column 6, line 48, delete "invention, that various" and insert --invention, various--.

Signed and Sealed this

Eighth Day of November, 1994

Attest:

BRUCE LEHMAN

*Attesting Officer*     Commissioner of Patents and Trademarks

UNITED STATES PATENT AND TRADEMARK OFFICE
CERTIFICATE OF CORRECTION

PATENT NO.   : B1 5,108,388
DATED        : April 28, 1992
INVENTOR(S)  : Stephen L. Trokel It is certified that error appears in the above-identified patent and that said Letters Patent is hereby corrected as shown below:

Column 1:
After numbered line 40, please insert --2. The method of claim 1 wherein said selected wavelength is 193 nanometers. --

Claim 8, Column 2:
Line 37, change "cornea" to --corneal--.

Claim 13, Column 3
Line 51, change "steepeining" to -- steepening--.

Claim 23, Column 5:
Line 57, change "cornea" to --corneal--.

Claim 33, Column 8:
Lines 13-14, delete "at a wavelength of 193 nanometers:" and insert therefore -- onto a predetermined area of corneal tissue; --.

Claim 49, Column 11:
Line 51, change "said diameter." to --said first diameter.--.

UNITED STATES PATENT AND TRADEMARK OFFICE
CERTIFICATE OF CORRECTION

PATENT NO. : B1 5,108,388
DATED : April 28, 1992
INVENTOR(S) : Stephen L. Trokel It is certified that error appears in the above-identified patent and that said Letters Patent is hereby corrected as shown below:

Claim 51, Column 12:
Line 27, change "said dimension." with --said first dimension."

Claim 63, Column 14:
Line 42, change "cornea ablative" to --cornea by ablative--.

Signed and Sealed this

Twelfth Day of June, 2001

*Attest:*

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO.   : 5,108,388
DATED        : April 18, 1992
INVENTOR(S)  : Stephen L. Trokel It is certified that error appears in the above-identified patent and that said Letters Patent is hereby corrected as shown below:

Column 1,
Line 15, delete "procedres" and insert -- procedures --;
Line 24, delete "regardles" and insert -- regardless --;
Line 34, delete ";" and insert -- , --;
Line 64, delete "interation" and insert -- interaction --;
Line 67, delete ".A" and insert new paragraph -- A new tissue ... --

Column 2,
Line 1, delete "ultravoilet" and insert -- ultraviolet --;
Line 5, insert "," after (nanometers);
Line 24, delete "photo-decomposition" and insert -- photodecomposition --;
Line 26, delete "utilizing far-" and insert -- utilizing a far- --;
Line 50, delete "and intensity";
Line 57, delete "drawing and" and insert -- drawings, and --;
Line 58, delete "DRAWING" and insert -- DRAWINGS --;
Line 60, delete "the drawing:" and insert -- the drawings: --.

Column 3,
Line 30, delete "repetitio" and insert -- repetition --;
Line 36, delete "either";
Line 40, delete "nevertheless, that" and insert -- nevertheless, that, --;
Line 41, delete "invention:" and insert -- invention --;
Line 45, delete "masks and that" and insert -- masks; and the --;
Line 65, delete "is pulses at" insert -- is pulsed at --;

Column 4,
Line 27, delete "110; and that in" and insert -- 110 and that, in --
Line 39, delete "of polymetal" and insert -- of polymethyl --;
Line 54, delete "use laser" and insert -- use, laser --;

UNITED STATES PATENT AND TRADEMARK OFFICE
CERTIFICATE OF CORRECTION

PATENT NO. : 5,108,388
DATED : April 18, 1992
INVENTOR(S) : Stephen L. Trokel

It is certified that error appears in the above-identified patent and that said Letters Patent is hereby corrected as shown below:

Column 5,
Line 12, delete "epthelium" and insert -- epithelium --
Line 32, delete "20. The result-" and insert -- 20. During the result- --;
Line 33, delete "photo-decomposition" and insert -- photodecomposition -- and delete "tissue are" and insert -- tissue is --;
Line 34, delete "by the direct" and insert -- by direct --;
Lines 38-40, delete "each photon provides the photo-chemical energy of the described apparatus and method directly breaks intramolecular" and insert -- each photon breaks intramolecular --;
Line 55, delete "lenght" and insert -- length --;
Line 61, delete "keratectomy as" and insert -- keratectomy, as --;

Column 6,
Line 11, delete "controlled filtering filtering" and insert -- controlled filtering --;
Line 13, delete "(b) A" and insert -- (b) a --;
Line 14, delete, "could be done" and insert -- to be done --;
Lines 15 and 16, delete "rod; (c) the Fibroptic rod delivery systems allows placement of the unit" and insert -- rod; and (c) placement of the unit --;
Line 19, delete "such biber" and insert -- such fiber --;
Line 34, delete "herein above" and insert -- hereinabove --;
Line 41, delete "it will thus be" and insert -- it will be obvious --;
Line 44, delete "apppended" and insert -- appended --;
Line 48, delete "invention, that various" and insert -- invention, various --.

Signed and Sealed this

First Day of March, 2005

JON W. DUDAS
*Director of the United States Patent and Trademark Office*

REEXAMINATION CERTIFICATE (4156th)

United States Patent [19]
Trokel

[11] B1 5,108,388
[45] Certificate Issued Sep. 19, 2000

[54] LASER SURGERY METHOD

[75] Inventor: Stephen L. Trokel, New York, N.Y.

[73] Assignee: Visx, Inc., Santa Clara, Calif.

Reexamination Request:
No. 90/004,889, Jan. 9, 1998

Reexamination Certificate for:
Patent No.: 5,108,388
Issued: Apr. 28, 1992
Appl. No.: 07/109,812
Filed: Oct. 16, 1987

Certificate of Correction issued Nov. 8, 1994.

Related U.S. Application Data

[63] Continuation of application No. 06/859,212, May 2, 1986, abandoned, which is a continuation of application No. 06/561,804, Dec. 15, 1983, abandoned.

[51] Int. Cl.$^7$ .................................................... A61N 5/06
[52] U.S. Cl. ..................... 606/5; 606/3; 606/13

[56] References Cited

U.S. PATENT DOCUMENTS

| | | |
|---|---|---|
| 3,330,182 | 7/1967 | Gerber et al. . |
| 3,828,188 | 8/1974 | Matula . |
| 3,828,788 | 8/1974 | Krasnov et al. . |
| 3,982,541 | 9/1976 | L'Esperance, Jr. . |
| 4,173,980 | 11/1979 | Curtin . |
| 4,461,294 | 7/1984 | Baron . |
| 4,485,499 | 12/1984 | Castlemann . |
| 4,538,608 | 9/1985 | L'Esperance, Jr. . |
| 4,648,400 | 3/1987 | Schneider et al. . |
| 4,665,913 | 5/1987 | L'Esperance . |
| 4,686,979 | 8/1987 | Gruen et al. . |
| 4,729,372 | 3/1988 | L'Esperance, Jr. . |
| 4,732,148 | 3/1988 | L'Esperance . |
| 4,744,360 | 5/1988 | Bath . |
| 4,769,963 | 9/1988 | Goldman et al. . |
| 4,784,135 | 11/1988 | Blum . |
| 4,825,865 | 5/1989 | Zelman . |
| 4,846,172 | 7/1989 | Berlin . |
| 4,973,330 | 11/1990 | Azema et al. . |
| 5,423,801 | 6/1995 | Marshall et al. . |
| 5,711,762 | 1/1998 | Trokel .......................................... 606/2 |
| 5,735,843 | 4/1998 | Trokel ........................................ 606/5 |

OTHER PUBLICATIONS

Deposition of Dr. Rangaswamy Srinivasan on Jan. 16, 1990 in Interference No. 102,026 (Trokel v. L'Esperance).

Affidavit of Louis J. Girard, prepared in connection with U.S. application Ser. No. 891,169 to L'Esperance, and executed Dec. 2, 1987.

Myopia Surgery, McMillan Publishing Co, Inc., New York, Toronto, London, Chapter 5 by W. Andrew Maxwell and Lee T. Nordan entitled "*Myopic Keratomileusis*," (1990) pp. 129–134.

*Ophthalmologie*, Louis Guillaumat, pp. 344 and 346 entitled "Pathologie Regionale Et Tissuelaire," publication date 1953.

(List continued on next page.)

*Primary Examiner*—Lee S. Cohen

[57] ABSTRACT

An argon-flouride excimer laser or other laser source capable of generating far-ultraviolet radiation at 193 nm is pulsed with energy densities of greater than 20 mj per cm$^2$ at a repetition rate up to 25 pulses per second to direct its radiation through a mask and onto corneal tissue, or other biological matter, to form a groove therein of predetermined configuration and depth by a process of ablative photodecomposition. The masks are formed with a slit, circular, crescent or other openings of widths between 30 and 800 microns, and may even be formed to provide a graded intensity center to edge. The mask is reflective or composed of or faced with an organic polymer to prevent heat build-up. Each micron of the depth of a 200 micron deep groove formed in corneal tissue, for example, resulted from the application of 1 joule per square centimeter of radiation, from a series of pulses delivered at intensities of between 100 mj and 200 mj per square centimeter and at a laser pulse rate of between 1 and 25 Hertz; the entire groove taking 100 seconds.

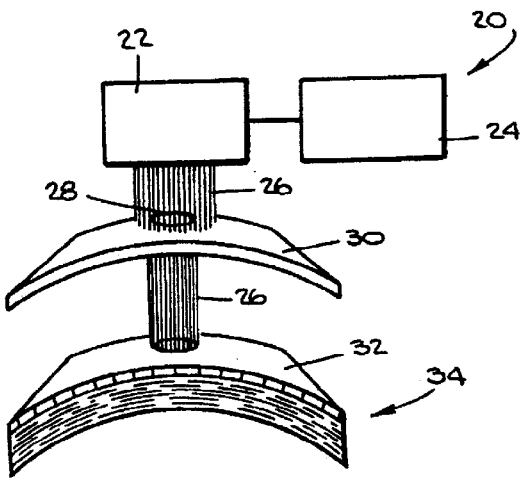

OTHER PUBLICATIONS

Article entitled "Lesion Duration and Curvature change in the Cornea Following Exposure to a Carbon Dioxide Laser," Mikesell et al. Report SAM–TR–79–26 (1979).
Article entitled "Reshaping the Cat Corneal Anterior Surface Using a High–Speed Diamond Frise," by Olson et al., Ophthalmic Surgery, (1980) pp. 784–786.
Article entitled "Refractive Keratoplasty—Microkeratome Evaluation", Binder et al., Arch Ophthalmol., vol. 100, (1982), pp. 802–806.
Article entitled "Excimer Lasers in Medicine", in Lasers and Applications, Muller (1988) pp. 85–89.
Wall Street Journal, Technology Section, Jan. 30, 1987, "Laser Shaping of Cornea Shows Promise at Correcting Eyesight".
Reprint from Laser Surg. Med., 6, 241, 1986, abstract entitled "Corneal surgery with an Er:YAG Laser at 2.94 um.," Wolbarsht et al.
The article entitled "Photoablative Reprofiling of the Cornea Using an Excimer Laser Photorefractive Keratectomy," Marshall et al., Lasers in Ophthalmology, vol. 1 No. 1 (1986), pp. 21–48.
The paper entitled "Quantitation of Corneal Ablation by Ultraviolet laser Light," Krueger and Trokel, Arch Ophthalmol. vol. 103, (1985), pp. 1741–1742.
The article entitled "Guest Editorial: Excimer lasers in Ophthalmology," Steiner et al., J. Cataract. Refract. Surg., vol. 15, (1989) pp. 369–370.
The article entitled "Safety Fears Focused on "healing"Laser", Hecht, New Scientist, vol. 134, No. 1825, Technology Section, Jun. 12, 1992, p. 18.
Statutory Declaration of Professor John Marshall, prepared in connection with an Opposition by Summit Technology, Inc. to European patent No. 0 218 427, and executed on Sep. 17, 1993.
Statutory Declaration of Professor Carmen A. Puliafito, prepared in connection with an Opposition by Summit Technology, Inc. to European patent No. 0 218 427, and executed on Aug. 30, 1993.
Statutory Declaration of Dr. Theo Seiler, prepared in connection with an Opposition by Summit Technology, Inc. to European patent No. 0 218 427, and executed on Aug. 5, 1993.
World Wide Web page http://www.mdweb.com/uslaser/prk.htm, undated.
World Wide Web page http://www.mdweb.com/uslaser/prk.htm, dated May 6, 1998, printed pp. 1–21.
Article entitled "Maddox Excimer Laser Center PRK—The PRK Experience" at World Wide Web page http://www.escimernet.com/MPRKbody.htm dated May 6, 1998, printed pp. 1–21.
Advanced Techniques in Ophthalmic Microsurgery, Vol. Two Corneal Surgery. Girard (1981), pp. 84, 101, 107–110, 114, 116, 123, 125–133, 143–171.
Affidavit of Stephen L. Trokel, prepared in connection with opposition to European application No. 86307420.9–2305/0218427 and 87306826.6–2302/0257836, and executed on Dec. 5, 1995.
Book entitled *Beyond Glasses!*, Armstrong, UC Books (1997), Title page and copyright page, pp. 4 and 5.
Printout of a database search on LEXIS for articles citing the Dec. 15, 1983 Trokel et al. article.
Apr. 20, 1998 letter from Jan Wetzel La Vigne to Larry Woody at VISX Corporation.
The book entitled *"Excimer Lasers in Ophthalmology"*, McGhee et al., Butterworth–Heinemann press, 1997, copy of the title page, the copyright page, and the table of contents pages.
Article entitled "Laser Interactions With the Cornea," Krauss et al. Survey of Ophthalmology, vol. 31, No. 1, Jul.–Aug. (1986), pp. 37–53.
"An Acute Light and Electron Microscopic Study of Ultraviolet 193–nm Excimer Laser Corneal Incisions," Berns et al., Ophthalmology, vol. 95, No. 10, (1988), pp. 1422–1433.
"Excimer Laser Radial Keratotomy in the Living Human Eye: A Preliminary Report," Tenner et al., J. of Refractive Surgery, vol. 4, No. 1, (1988), pp. 5–8.
The article entitled "In Vivo Experiments With the Excimer laser—Technical Parameters and Healing Processes," Seiler et al. Ophthalmologica, vol. 192 (1986), pp. 65–70.
The paper entitled "Wound Healing Following Excimer Laser Radical Keratotomy," Rosa et al. J. Cataract. Refract. Surg. vol. 14, (1988), pp. 173–179.
The interim report "Ocular Effects of Ultraviolet Laser Radiation," Zuclich et al., Report No. SAM–TR–74–32 (1974).
The article entitled "Quantitative and Ultrastructural Studies of Excimer laser Ablation of the Cornea at 193 and 248 Nanometers," Puliafito et al. Lasers in Surgery and Medicine, vol. 7 (1987), pp. 155–159.
Report entitled "Corneal Damage Thresholds for Hydrogen Flouride and Deuterium Fluoride Chemical Lasers," report No. SAM–TR–73–51 (1972).
The article entitled "Human Excimer Laser Keratectomy: Short–Term Histopathology," L'Esperance et al. Journal of Refractive surgery, vol. 4 No. 4 (1988), pp. 118–124.
The article entitled "Traumatic Corneal Abrasions Following Photorefractive Keratectomy" Salz, Refractive and Corneal Surgery, vol. 10, (1994), pp. 36–37.
Dialog abstract 04240920 84246771 by Yamaguchi et al. entitlted "The Ultrastructure of Well Healed Lenticles in Keratomileusis" (Dec. 1983).
Keates et al. "Carbon Dioxide Laser Beam Control for Corneal Surgery" Ophthalmic Surgery vol. 12 No. 2 (1981), pp. 117–122.
Dialog abstract No. 09008031 97235748 (1997) by Bohm et al. entitled "Biomechanische Untersuchung der Hornhautstabilitat nach photorefraktiver Keratektomie".
Dialog abstract No. 04754808 (1982) by Avetisov, entitled "An Experimental Study of the Possibility of Using Carbon Dioxide Laser for Changing the Cornea Refraction".
The first 37 CFR 1.639(b) declaration of Dr. Myron L. Wolbarsht, in support of the party L'Esperance's first and second motions under 37 CFR 1.633(a), prepared in connection with the Trokel v. L'Esperance interference No. 102,026, and executed Jan. 27, 1989.
The second 37 CPR 1.639(b) declaration of Dr. Myron L. Wolbarsht, in support of the party L'Esperance's replies in the Trokel v. L'Esperance interference No. 102,026, and executed Mar. 3, 1989.
Paper No. 102 entitled "Decision on Preliminary Motions" in the Trokel v. L'Esperance interference No. 102,026.
The article entitled "Cytotoxicity and Mutagenicity Unscheduled DNA Synthesis of Low Intensity, 248 and 193 nm Excimer laser Radiation in Mammalian Cells," Green et al., Cancer Research, vol. 47 (1987), pp. 410–413.
The article entitled "Mutagenic Potential of a 193–nm Excimer Laser on Fibroblasts in Tissue Culture," Trentacoste et al. Ophthalmology, vol. 94 (1987), pp. 125–129.

The article entitled "Unscheduled DNA Synthesis in Human Skin After In Vitro Ultraviolet–Excimer laser Ablation," Green et al., Journal of Investigative Dermatology, Vo. 89 (1987), pp. 201–204.
The article entitled "Human Excimer Laser Lamellar keratectomy," Taylor et al, Ophthalmology, vol. 96 (1989), pp. 654–664.
The article entitled "Ocular Damage Induced By Near Ultraviolet Laser Radiation," Zuclich et al., Investigation Ophthalmology, vol. 15 (1976), pp. 760–764.
Printout of IBM patent server web page citing 13 United States patents that reference United States patent No. 5,108, 388.
Printout of IBM patent server web page citing 26 United States patents that reference "Trokel et al." and "1983", the indicia identifying the seminal Trokel et al. 1983 publication.
Printout of citations and abstracts of two articles by Barraquer dated 1972 and 1966 respectively.
Statement of Dr. Reinhardt Thyzel prepared in connection with VISX Incorporated v. Nidek Co., Ltd. in the High Court of Justice, Chancery Division, England, executed Nov. 7, 1998.
Miller et al. "Intraocular Carbon Dioxide Laser Photocautery" Arch Ophthalmology vol. 97, Nov. 1979, pp. 2157–2162.
Allan et al. "Laser Microsclerostomy For Primary Open Angle Glaucoma: A Review of Laser Mechanisms and Delivery Systems," Eye (1992) 6, 257–66.
Peyman, et al. "Role of the $CO_2$ Laser in Chorioretino–iridocyclectomy" Ophthalmic Surgery vol. 12 No. 6 (1981), pp. 426–431.
Goldbaum et al. "The $CO_2$ Laser in Oculoplastic Surgery" Diagnostic and Surgical Techniques vol. 42 No. 3 Nov.–Dec. 1997, pp. 255–266.
Krauss et al. "Lasers in Ophthalmology" Lasers in Surgery and Medicine 17 (1995), pp. 102–159.
Yoshimoto et al. "Vitreous morphology after carbon dioxide laser irradiation" Graefe's Arch Clin Exp Opthalmol 221 (1984), pp. 276–281.
Ren et al. "Laser refractive surgery: a review and current status" Optical Engineering vol. 34 No. 3, pp. 642–660.
Thompson et al. "Therapeutic and Diagnostic Application of Lasers in Ophthalmology" Proceedings of the IEEE vol. 80, No. 6, Jun. 1992, pp. 838–860.
Loertscher et al. "Noncontact Trephination of the Cornea Using a Pulsed Hydrogen Fluoride Laser" American Journal of Ophthalmology 104 Nov. 1987, pp. 471–475.
Loertscher et al. "Preliminary Report on corneal Incisions Created by a Hydrogen Fluoride laser" American Ournal of Ophthalmology 102 Aug. 1986, pp. 217–221.
Seiler et al. "Side effects in excimer cornal surgery" Graefe's Arch Clin Exp Opthalmol 226 (1988), pp. 273–276.
Peyman et al. "Effects of erbium: YAG laser on ocular structures" International Ophthalomology 10 (1987), pp. 245–253.
Seiler et al. "Excimer Laser Photorefractive Keratectomy" Survey of Ophthalmology vol. 40 No. 2 Sep.–Oct. 1995, pp. 89–118.
Puliafito et al. "Excimer Laser Ablation of the Cornea and lens" Ophthalmology vol. 92 No. 6 (1985), pp. 741–748.
File history of United States application serial No. 731,121 filed May 6, 1985.

The book entitled "Excimer Lasers in Ophthalmology", McGhee et al., Butterworth–Heinemann press, 1997, copy of the cover, the copyright page, and p. 50.
Paper No. 234 mailed Nov. 6, 1997 in Gruen v. Linsker v. Grundfest, interference No. 102,459 p. 68 line 22 to p. 70 line 16.
Transcript of the testimony of Dr. Keates in Summit Technology & VISX Inc., FTC Matter No. D09286, Trial Vol. No. 5, Dec. 18, 1998.
Business plan of Dr. Keates Exhibits Keates No. 12, Respondent Exhibit No. RX–1422, in Summit Technology & VISX Inc., FTC Matter No. D09286.
Initial Decision of Judge Levin in the matter of VISX, Incorporated, Docket No. 9286, in the Federal Trade Commission.
Krauss et al., "Laser interactions With the Cornea," Survey of Ophthalmology vol. 31, p. 37 (1986).
Loertscher et al., entitled "Noncontact Trephination of the Cornea Using a Pulsed Hydrogen Fluoride Laser," American Journal of Ophthalmology, vol. 104, p. 471 (1987).
Loertscher et al., entitled "Preliminary Report on Corneal Incisions Created by a Hydrogen Fluoride laser," American Journal of Ophthalmology, vol. 102, p. 217 (1987).
Figure illustrating Beckman et al.'s limbectomy procedure.
Figure illustrating Beckman et al.'s partial penetrating keratectomy.
Figure illustrating Beckman et al.'s penetrating annular keratectomy.
Maurice, "the Structure and Transparency of the Corena," J. Physiol. pp. 263–286 (1957).
Goldman et al., "Structural Alterations Affecting Transparency in Swollen human Corneas," Investigative Ophthalmology, pp. 501–519 (1968).
Farrell et al., "Wavelength Dependence in Light Scattering in Normal and Cold Swollen Rabbit Corneas and Their Structural Implications," J. Physiol. pp. 589–612 (1973).
Scott JE, "Proteoglycan: collegen interaction and corneal ultrastructure," Biochem Soc Trans (1991) 19:887–81.
Forrester JV, Dick AD, McMenamin PG, Lee WR, "The Eye: Basic Sciences in Practice," WB Saunders, London, (1996), 14–18, 101–2, 158–67.
Maurice, "The Use of Permeability Studies in the investigation of Submicroscope Structure," *Structure of the Eye*, Edited by Smelser, Academic Press, pp. 381–391 (1961).
A copy of the claims pending in the '207 application organized by restricted groups I–X.
Trokel et al., "Excimer Laser Surgery of the Cornea," American Journal of Ophthalmology, vol. 96, pp. 710–715 (1983).
Taboada et al., "An Extreme Sensitivity in the Corneal Epithelium To Far UV ArF Excimer Laser Pulses," Proc. Of the Scientific Program Aerospace medical Association, 1981 meeting, pp. 98–99 (referred to as the "Taboada et al. 193 nm publication").
Taboada, J., Mikesell, G. W. Jr., and Reed, R. D., "Response to the Corneal Epithelium to KrF Excimer Laser Pulses," (referred to as the "Taboada et al. 248 nm publication").
A copy of the office action mailed Feb. 26, 1997 in the Trokel '741 application.
Seiler et al., "Side Effects in Excimer Corneal surgery: DNA Damage as a Result of 193 nm Excimer laser Radiation," Graefe's Archive for Clinical and Experimental ophthalmology (1988), pp. 273–276.

Boruchoff et al., "Corneal Abrasions, Contusions, Lacerations, and Perforations," Current Ocular Therapy, (1989), pp. 299–300.

Frank W. Newell's textbook, *Ophthalmoloy; Principles and Concepts* (4$^{th}$ Ed. 1978), pp. 80–112, title page, and copyright page.

Waring, "Developments and Evaluation of Refractive Surgical Procedures" Journal of Refractive Surgery, Aug., 1987, vol. 3, No. 4, (Publication of Dr. Waring's 1987 Lans Distinguished Refractive Surgery Lecture).

Pp. 2042–2057 from Dr. Keith Thompson's testimony in the FTC action, matter No. D09286 on Jan. 4, 1999 and Waring, "Developments and Evaluation of Refractive Surgical Procedures" Journal of Refractive Surgery, Aug. 1987, vol. 3, No. 4, (Publication of Dr. Waring's 1987 Lans Distinguished Refractive Surgery Lecture).

Dr. Keith Thompson's testimony in the FTC action, matter No. D09286 on Jan. 4, 1999, pp. 1762–2167 and attached index.

Declaration of Ralph Linsker under 35 USC 132 in Blum et al. application serial No. 448,123, filed Dec. 9, 1992, date stamped Aug. 16, 1984.

Paper filed Apr. 16, 1984 in Blum et al. application No. 448,123 entitled "Citation of References Under 37 C.F.R. 1.56" including a list of references identifying the Taboada et al. 248 nm publication as reference AR and the Taboada et al. 193 nm publication as reference AT.

Amendment filed Aug. 16, 1984 in the Blum et al. application 448,123.

A copy of correspondence from Dr. Taboada to Dr. Munnerlyn containing a letter from Dr. Taboada to Dr. Munnerlyn dated Apr. 3, 1990 and the feasibility study referred to in the letter.

Definition of "scar tissue"—Dictionary of Scientific and Technical Terms, second edition, p. 1410 which, along with the title and copyright pages of that dictionary ("[c]ontracted, dense connective tissue that is formed by the healing process of a wound or diseased tissue.").

Definition of Photocoagulation—*Dorland's Illustrated Medical Dictionary*, title page, copyright page, and page 1286 (condensation of protein material by the controlled use of an intense beam of light (e.g., xenon arc light or argon laser). . . ).

Beckman et al., Limbectomies, Keratectomies, and Keratostomies Performed With a Rapid–Pulsed Carbon Dioxide Laser Am. J. Ophthalmology, 1277–1283 (1971).

37 CFR 1.131 declaration of Dr. Stephen Trokel submitted in application serial No. 08/474,243.

Form SE Registration No. 1–272–511 registering the copyright Trokel et al. publication, dated Dec. 29, 1983.

37 CFR 1.132 declaration of Susan Corrigan.

37 CFR 1.132 declaration of Terry Burkhold.

Deposition of Bodil Braren on Jan. 25, 1990 in interference No. 102,026 (Trokel v. L'Esperance).

Declaration of Dr. James J Wynne filed Aug. 21, 1985 in the Blum et al. application 448,123.

Sisakyan et al., "New Principles for Laser Beam management in Ophthalmologic Surgery," Ophthal. Proc. Series, vol. 36, Junk Publishers, the Hague (1984).

Copies of the portions of the transcript of an ITC proceeding Inv. No. 337–TA–419 that are publicly available.

A summary of a decision by a judge in the Inv. No. 337–TA–419 ITC proceeding.

OUII Petition for Review of Final Initial Determination Inv. No. 337–TA–419.

Response of the OUII to Petitions of Other Parties for Review of Final Initial Determinations Inv. No. 337–TA–419.

Initial Determination Inv. No. 337–TA–419.

Richard H. Keates, Carbon Dioxide Laser Beam Control for Corneal Surgery, 12 Opththalmic Surgery, Feb. 1981, pp. 117–122.

Hugh Beckman et al., Limbectomies, Keratectomies, and Keratostomies Performed with a Rapid Pulsed Carbon Dioxide Laser, 71 Am. J. Ophthalmology, Jun. 1971, pp. 1277–1283.

Gholam A. Peyman et al., Modification of Rabbit Corneal Curvature with Use of Carbon Dioxide Laser Burns, 11 Ophthalmic Surgery, May 1980, pp. 325–329.

Rebuttal Expert Report of Dr. Michael S. Feld Re: Validity; Civil Action No. 95–524–SLR; United States District Court for the District of Delaware; Dec. 30, 1996.

Report of James H. Brannon Pursuant to Federal Rule of Civil Procedure 26; Civil Action No. 95–524 SLR; United States District Court for the District of Delaware; Dec. 9, 1996.

Rebuttal Expert Report of Dr. Jack Feinberg Re: Validity; Civil Action No. 95–524–SLR; United States District Court for the District of Delaware; Dec. 23, 1996.

Deposition of Alain Azema; Civil Action No. 95–524–SLR; United States District Court for the District of Delaware; Sep. 17, 1996.

Rebuttal Expert Report of Roger F. Steinert, M.D. Re: Validity; Civil Action No. 95–524–SLR; United States District Court for the District of Delaware; Dec. 30, 1996.

Complaint to Order Correction of Patent and for Other Relief, Dated Jul. 2, 1997. (John Taboada, Plantiff).

Facsimile letter dated Jun. 7, 1994 from Howard L. Milhench, attorney for VISX Corporation, to the European patent office containing applicant's preliminary response to an opposition by Summit Technology, Inc. to European patent application No. 86307420.9–2305/021842.

Paper in European patent application Nos. 86307420.9–2305/0218427 and 87306826.6–2302/0257836 titled "Affidavit of Stephen L. Trokel" Sworn on Dec. 5, 1995.

Form EPO 2042 dated Dec. 29, 1995 having reference No. J.17848 in European patent application No. 86307420.9–2302/0218427.

Facsimile letter dated Feb. 8, 1995 from Howard L. Milhench, attorney for VISX Corporation, to the European patent office containing applicant's preliminary response to (1) an opposition by Firma Carl Zeiss and (2) an opposition by Summit Technology, Inc. to European patent application No. 86304097.8(247260).

Facsimile letter dated Jun. 2, 1994 from Howard L. Milhench, attorney for VISX Corporation, to the European patent office containing VISX's preliminary response to (1) an opposition by Firma Carl Zeiss and (2) an opposition by Summit Technology, Inc. to European patent application No. 87306826.6–2212/0257836.

Letter dated Sep. 22, 1994 from Howard L. Milhench, attorney for VISX Corporation, to the European patent office containing applicant's preliminary response to (1) an opposition by Firma Carl Zeiss and (2) an opposition by Summit Technology, Inc. to European patent application No. 87310283.4–0274205.

Facsimile message dated Dec. 23, 1991 from Howard L. Milhench, attorney for VISX Corporation, to the European patent office containing VISX's observations regarding (1) an opposition by Synthelabo, Paris (FR) and (2) an opposition by Zeiss, Oberkochen (DE) to European patent application No. 896304315.4–2305.

"Ocular damage induced by near–ultraviolet laser radiation", Zuclich et al., *Investigative Ophthalmology*, Sep. 1976 pp. 760–764.

"Ocular Effects of a 325 nm Ultraviolet Laser", Ebbers, et al., *American Journal of Optometry and Physiological Optics*, Mar. 1975 pp. 216–223.

"Thresholds and Mechanisms of Retinal Damage From a White–Light Laser", Reed et al., *Health Physics*, Jul., 1980, pp. 33–39.

"Retinal tissue damage induced by 6–psec 530–nm laser light pulses", Bruckner et al., *Applied Optics*, Feb. 1982, pp. 365–367.

"Ocular tissue damage due to ultrashort 1060–nm light pulses from a mode–locked Nd:glass laser", Taboada et al., *Applied Optics*, Aug. 1975, pp. 1759–1761.

"Ocular hazard from uv laser exhibiting self–mode–locking", Zuclich et al., *Applied Optics*, May 1978, pp. 1482–1484.

"Production of Cataracts in Rabbits with the Ultraviolet Laser", MacKeen et al., *Ophthal. Res.* 1973, pp. 317–324.

Complaint Docket No. 9286 in the Matter of Summit Technology, Inc. a Corporation and VISX, Inc. a Corporation, Before the Federal Trade Commission.

"Basis of Refractive Keratoplasty" by Barraquer, Arch. Soc. Offal. Optom (1967), pp. 21–68, except for pp. 22 and 42.

"Lesion Duration and Curvature change in the Cornea Following Exposure to a Carbon Dioxide Laser," Mikesell et al. Report SAM–TR–79–26 (1979).

DE 3148748 A1 (German patent publication to Karp) (twelve pages).

English language translation of DE31 48 748 A1 to Karp (ten pages).

"Reshaping the Cat Corneal Anterior Surface Using a High––speed Diamond Fraise," Olson et al., (1980) (three pages).

Testimony of Richard H. Keates in In re Summit Tech., Inc. et al., No. 9286 (F.T.C.).

Testimony of Stephen L. Trokel in In re Summit Tech., Inc. et al., No. 9286 (F.T.C.).

Expert report of Neal A. Sher, M.D., dated Nov. 2, 1998.

Expert report of Neal A. Sher, M.D., dated Nov. 13, 1998 (different content).

Expert report of Massoud Motamedi, Ph.D., dated Nov. 2, 1998.

George O. Waring, III, *Development & Eval. of Refractive Surgical Procedures* (1987).

Draft article with editor's notes, Stephen L. Trokel et al., *Excimer Laser Surgery of the Cornea*.

Copy of YAG Laser Ophthalmic Microsurgery, edited by Stephen L. Trokel, M.D., copywrite 1983 by Appleton–Century–Crofts.

Mueller, F.O. and P. O'Neill, "Some Experiments on Corneal Grinding," Exptl. Eye Res. 6:42–47 (1967).

Front pages of 20 District Court Cases Involving the Subject Patent.

Amended Answer and Counter Claim in Pillar Point Partners et al. V. Dishler et al.

Complaint in the Mater of Summit Technology, Inc. and VISX, Inc.

Amended Complaint in Taboada v. Trokel et al.

Amended Answer in Pillar Point Partners et al. v. Dulaney et al.

"Some Experiments on Corneal Grinding" Experimental Eye Res. 6:42–47 (1967).

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 3–5 are determined to be patentable as amended.

Claim 2, dependent on an amended claim, is determined to be patentable.

New claims 6–65 are added and determined to be patentable.

1. A method for producing a surgical excision of controlled depth and shape in a cornea by ablative photochemical decomposition of corneal tissue without thermal damage to the corneal tissue, said method comprising the steps of:
   (a) generating a laser beam in the far ultraviolet region of the energy spectrum and at a wavelength selected to produce ablative photochemical decomposition of corneal tissue without thermal damage to the corneal tissue [and];
   (b) directing said radiation in a controlled manner onto said corneal tissue to induce ablative photochemical decomposition thereof in a volumetric removal of said corneal tissue without thermal heating to create a surgical excision of controlled depth and shape with depth penetration into the stroma; and
   (c) *wherein the ablation overlaps the optically used area of the cornea.*

3. A method for producing a surgical excision of controlled depth and shape in a cornea by ablative photochemical decomposition of corneal tissue without thermal damage to the corneal tissue, said method comprising the steps of:
   (a) generating a laser beam at a wavelength of 193 nanometers;
   (b) directing said laser beam onto a predetermined area of corneal tissue;[and]
   (c) controlling said laser beam so as to induce ablative photochemical decomposition of said corneal tissue in a volumetric removal of said corneal tissue without thermal damage to said corneal tissue to create a surgical excision of controlled depth and shape with depth penetration into the stroma; and
   (d) *wherein the ablation overlaps the optically used area of the cornea.*

4. The method of changing optical properties of an eye by operating solely upon the anterior surface of the cornea of the eye, which method comprises selective ultraviolet irradiation and attendant ablative photodecomposition of the anterior surface of the cornea in a volumetric removal of corneal tissue and with depth penetration into the stroma and to a predetermined curvature profile, *and wherein the ablation overlaps the optically used area of the cornea.*

5. The method of using an ultraviolet laser to change the optical properties of an eye, which method comprises adjusting the intensity of laser beam projection to a level at which laser beam projection onto the anterior surface of the cornea of the eye will result in corneal-tissue ablation per unit time which is but a fraction of a predetermined maximum ablation depth into the stroma of the cornea, [and] directing the laser beam at the anterior surface of the cornea in a controlled manner to create at least one excision in the anterior surface of the cornea relative to the optic axis thereof by volumetric removal of corneal tissue in the course of ablative photodecomposition of the stroma causing a redefinition of the anterior surface of the cornea; *and wherein the ablation overlaps the optically used area of the cornea.*

6. *A method for producing a surgical excision of controlled depth and shape in a cornea by ablative photochemical decomposition of corneal tissue without thermal damage to the corneal tissue, said method comprising the steps of:*
   *(a) generating a laser beam in the far ultraviolet region of the energy spectrum and at a wavelength selected to produce ablative photochemical decomposition of corneal tissue without thermal damage to the corneal tissue;*
   *(b) directing said radiation in a controlled manner onto said corneal tissue to induce ablative photochemical decomposition thereof in a volumetric removal of said corneal tissue without thermal heating to create a surgical excision of controlled depth and shape with depth penetration into the stroma; and*
   *(c) wherein said step of directing comprises ablating more tissue centrally than peripherally throughout the optically used area of the cornea to effect a refractive correction.*

7. *The method of claim 6 wherein said selected wavelength is 193 nanometers.*

8. *A method for producing a surgical excision of controlled depth and shape in a cornea by ablative photochemical decomposition of corneal tissue without thermal damage to the cornea tissue, said method comprising the steps of:*
   *(a) generating a laser beam at a wavelength of 193 nanometers;*
   *(b) directing said laser beam onto a predetermined area of corneal tissue;*
   *(c) controlling said laser beam so as to induce ablative photochemical decomposition of said corneal tissue in a volumetric removal of said corneal tissue without thermal damage to said corneal tissue to create a surgical excision of controlled depth and shape with depth penetration into the stroma; and*
   *(d) wherein said step of controlling comprises ablating more tissue centrally than peripherally throughout the optically used area of the cornea to effect a refractive correction.*

9. *The method of changing optical properties of an eye by operating solely upon the anterior surface of the cornea of the eye, which method comprises a step of selective ultraviolet irradiation and attendant ablative photo decomposition of the anterior surface of the cornea in a volumetric removal of corneal tissue and with depth penetration into the stroma and to a predetermined curvature profile, and*
   *wherein said step of selective ultraviolet irradiation comprises ablating more tissue centrally than peripherally throughout the optically used area of the cornea to effect a refractive correction.*

10. *The method of using an ultraviolet laser to change the optical properties of an eye, which method comprises the steps of:*
    *adjusting the intensity of laser beam projection to a level at which laser beam projection onto the anterior sur-* face of the cornea of the eye will result in corneal-tissue ablation per unit time which is but a fraction of a predetermined maximum ablation depth into the stroma of the cornea;

directing the laser beam at the anterior surface of the cornea in a controlled manner to create at least one excision in the anterior surface of the cornea relative to the optic axis thereof by volumetric removal of corneal tissue in the course of ablative photo decomposition of the stroma causing a redefinition of the anterior surface of the cornea; and wherein said step of directing comprises ablating more tissue centrally than peripherally throughout the optically used area of the cornea to effect a refractive correction.

11. A method for producing a surgical excision of controlled depth and shape in a cornea by ablative photochemical decomposition of corneal tissue without thermal damage to the corneal tissue, said method comprising the steps of:

(a) generating a laser beam in the far ultraviolet region of the energy spectrum and at a wavelength selected to produce ablative photochemical decomposition of corneal tissue without thermal damage to the corneal tissue;

(b) directing said radiation in a controlled manner onto said corneal tissue to induce ablative photochemical decomposition thereof in a volumetric removal of said corneal tissue without thermal heating to create a surgical excision of controlled depth and shape with depth penetration into the stroma; and (c) wherein said step of directing comprises steepening the cornea by ablating more tissue peripherally than centrally throughout the optically used area of the cornea to effect a refractive correction.

12. The method of claim 11 wherein said selected wavelength is 193 nanometers.

13. A method for producing a surgical excision of controlled depth and shape in a cornea by ablative photochemical decomposition of corneal tissue without thermal damage to the corneal tissue, said method comprising the steps of:

(a) generating a laser beam at a wavelength of 193 nanometers;

(b) directing said laser beam onto a predetermined area of corneal tissue;

(c) controlling said laser beam so as to induce ablative photochemical decomposition of said corneal tissue in a volumetric removal of said corneal tissue without thermal damage to said corneal tissue to create a surgical excision of controlled depth and shape with depth penetration into the stroma; and (d) wherein said step of controlling comprises steepeining the cornea by ablating more tissue peripherally than centrally throughout the optically used area of the cornea to effect a refractive correction.

14. The method of changing optical properties of an eye by operating solely upon the anterior surface of the cornea of the eye, which method comprises a step of selective ultraviolet irradiation and attendant ablative photo decomposition of the anterior surface of the cornea in a volumetric removal of corneal tissue and with depth penetration into the stroma and to a predetermined curvature profile, and wherein said step of selective ultraviolet irradiation comprises steepening the cornea by ablating more tissue peripherally than centrally throughout the optically used area of the cornea to effect a refractive correction.

15. The method of using an ultraviolet laser to change the optical properties of an eye, which method comprises the steps of:

adjusting the intensity of laser beam projection to a level at which laser beam projection onto the anterior surface of the cornea of the eye will result in corneal-tissue ablation per unit time which is but a fraction of a predetermined maximum ablation depth into the stroma of the cornea;

directing the laser beam at the anterior surface of the cornea in a controlled manner to create at least one excision in the anterior surface of the cornea relative to the optic axis thereof by volumetric removal of corneal tissue in the course of ablative photo decomposition of the stroma causing a redefinition of the anterior surface of the cornea; and wherein said step of directing comprises steepening the cornea by ablating more tissue peripherally than centrally throughout the optically used area of the cornea to effect a refractive correction.

16. A method for producing a surgical excision of controlled depth and shape in a cornea by ablative photochemical decomposition of corneal tissue without thermal damage to the corneal tissue, said method comprising the steps of:

(a) generating a laser beam in the far ultraviolet region of the energy spectrum and at a wavelength selected to produce ablative photochemical decomposition of corneal tissue without thermal damage to the corneal tissue;

(b) directing said radiation in a controlled manner onto said corneal tissue to induce ablative photochemical decomposition thereof in a volumetric removal of said corneal tissue without thermal heating to create a surgical excision of controlled depth and shape with depth penetration into the stroma; and (c) wherein said step of directing comprises shaping a central surface of the cornea involved in vision in situ by removing corneal tissue from the central surface of the cornea involved in vision to effect a refractive correction.

17. The method of claim 16 wherein said selected wavelength is 193 nanometers.

18. A method for producing a surgical excision of controlled depth and shape in a cornea by ablative photochemical decomposition of corneal tissue without thermal damage to the corneal tissue, said method comprising the steps of:

(a) generating a laser beam at a wavelength of 193 nanometers;

(b) directing said laser beam onto a predetermined area of corneal tissue;

(c) controlling said laser beam so as to induce ablative photochemical decomposition of said corneal tissue in a volumetric removal of said corneal tissue without thermal damage to said corneal tissue to create a surgical excision of controlled depth and shape with depth penetration into the stroma; and (d) wherein said step of controlling comprises shaping a central surface of the cornea involved in vision in situ by removing corneal tissue from the central surface of the cornea involved in vision to effect a refractive correction.

19. The method of changing optical properties of an eye by operating solely upon the anterior surface of the cornea of the eye, which method comprises the step of:

selective ultraviolet irradiation and attendant ablative photo decomposition of the anterior surface of the cornea in a volumetric removal of corneal tissue and with depth penetration into the stroma and to a predetermined curvature profile; and wherein said step of selective ultraviolet irradiation comprises shaping a central surface of the cornea involved in vision in situ by removing corneal tissue from the central surface of the cornea involved in vision to effect a refractive correction.

20. The method of using an ultraviolet laser to change the optical properties of an eye, which method comprises the steps of:

adjusting the intensity of laser beam projection to a level at which laser beam projection onto the anterior surface of the cornea of the eye will result in corneal-tissue ablation per unit time which is but a fraction of a predetermined maximum ablation depth into the stroma of the cornea;

directing the laser beam at the anterior surface of the cornea in a controlled manner to create at least one excision in the anterior surface of the cornea relative to the optic axis thereof by volumetric removal of corneal tissue in the course of ablative photo decomposition of the stroma causing a redefinition of the anterior surface of the cornea; and wherein said step of directing comprises shaping a central surface of the cornea involved in vision in situ by removing cornea tissue from the central surface of the cornea involved in vision to effect a refractive correction.

21. A method for producing a surgical excision of controlled depth and shape in a cornea by ablative photochemical decomposition of corneal tissue without thermal damage to the corneal tissue, said method comprising the steps of:

(a) generating a laser beam in the far ultraviolet region of the energy spectrum and at a wavelength selected to produce ablative photochemical decomposition of corneal tissue without thermal damage to the corneal tissue;

(b) directing said radiation in a controlled manner onto said corneal tissue to induce ablative photochemical decomposition thereof in a volumetric removal of said corneal tissue without thermal heating to create a surgical excision of controlled depth and shape with depth penetration into the stroma; and (c) wherein said step of directing comprises shaping a central surface area of the cornea involved in vision by impinging different regions of the central surface area of the cornea with different pulses of said laser beam during the course of a laser surgical procedure, which thereby grades the central surface area of the cornea to effect a refractive correction.

22. The method of claim 31 wherein said selected wavelength is 193 nanometers.

23. A method for producing a surgical excision of controlled depth and shape in a cornea by ablative photochemical decomposition of corneal tissue without thermal damage to the corneal tissue, said method comprising the steps of:

(a) generating a laser beam at a wavelength of 193 nanometers;

(b) directing said laser beam onto a predetermined area of corneal tissue;

(c) controlling said laser beam so as to induce ablative photochemical decomposition of said corneal tissue in a volumetric removal of said corneal tissue without thermal damage to said corneal tissue to create a surgical excision of controlled depth and shape with depth penetration into the stroma; and (d) wherein said step of controlling comprises shaping a central surface area of the cornea involved in vision by impinging different regions of the central surface area of the cornea with different pulses of said laser beam during the course of a laser surgical procedure, which thereby grades the central surface area of the cornea to effect a refractive correction.

24. The method of changing optical properties of an eye by operating solely upon the anterior surface of the cornea of the eye, which method comprises the step of:

selective ultraviolet irradiation and attendant ablative photo decomposition of the anterior surface of the cornea in a volumetric removal of corneal tissue and with depth penetration into the stroma and to a predetermined curvature profile, and wherein said step of selective ultraviolet irradiation comprises shaping a central surface area of the cornea involved in vision by impinging different regions of the central surface area of the cornea with different pulses of said ultraviolet irradiation during the course of a laser surgical procedure, which thereby grades the central surface area of the cornea to effect a refractive correction.

25. The method of using an ultraviolet laser to change the optical properties of an eye, which method comprises the steps of:

adjusting the intensity of laser beam projection to a level at which laser beam projection onto the anterior surface of the cornea of the eye will result in corneal-tissue albation per unit time which is but a fraction of a predetermined maximum ablation depth into the stroma of the cornea;

directing the laser beam at the anterior surface of the cornea in a controlled manner to create at least one excision in the anterior surface of the cornea relative to the optic axis thereof by volumetric removal of corneal tissue in the course of ablative photo decomposition of the stroma causing a redefintion of the anterior surface of the cornea; and wherein said step of directing comprises shaping a central surface area of the cornea involved in vision by impinging different regions of the central surface area of the cornea with different pulses of said laser beam during the course of a laser surgical procedure, which thereby grades the central surface area of the cornea to effect a refractive correction.

26. A method for producing a surgical excision of controlled depth and shape in a cornea by ablative photochemical decomposition of corneal tissue without thermal damage to the corneal tissue, said method comprising the steps of:

(a) generating a laser beam in the far ultraviolet region of the energy spectrum and at a wavelength selected to produce ablative photochemical decomposition of corneal tissue without thermal damage to the corneal tissue;

(b) directing said radiation in a controlled manner onto said corneal tissue to induce ablative photochemical decomposition thereof in a volumetric removal of said corneal tissue without thermal heating to create a surgical excision of controlled depth and shape with depth penetration into the stroma; and (c) wherein the surface immediately below said excision of controlled depth and shape resulting from the ablation defines a convex surface of the optically used area of the cornea.

27. The method of claim 26 wherein said selected wavelength is 193 nanometers.

28. A method for producing a surgical excision of controlled depth and shape in a cornea by ablative photochemical decomposition of corneal without thermal damage to the corneal tissue, said method comprising the steps of:

(a) generating a laser beam at a wavelength of 193 nanometers;

(b) directing said laser beam onto a predetermined area of corneal tissue;

(c) controlling said laser beam so as to induce ablative photochemical decomposition of said corneal tissue in a volumetric removal of said corneal tissue without thermal damage to said corneal tissue to create a surgical excision of controlled depth and shape with depth penetration into the stroma; and (d) wherein the surface immediately below said excision of controlled depth and shape resulting from the ablation defines a convex surface of the optically used area of the cornea.

29. The method of changing optical properties of an eye by operating solely upon the anterior surface of the cornea of the eye, which method comprises selective ultraviolet irradiation and attendant ablative photo decomposition of the anterior surface of the cornea in a volumetric removal of corneal tissue and with depth penetration into the stroma and to a predetermined curvature profile, and wherein the surface immediately below said volumetric removal of corneal tissue resulting from the ablation defines a convex surface of the optically used area of the cornea.

30. The method of using an ultraviolet laser to change the optical properties of an eye, which method comprises the steps of:

adjusting the intensity of laser beam projection to a level at which laser beam projection onto the anterior surface of the cornea of the eye will result in corneal-tissue ablation per unit time which is but a fraction of a predetermined maximum ablation depth into the stroma of the cornea;

directing the laser beam at the anterior surface of the cornea in a controlled manner to create at least one excision in the anterior surface of the cornea relative to the optic axis thereof by volumetric removal of corneal tissue in the course of ablative photo decomposition of the stroma causing a redefinition of the anterior surface of the cornea; and wherein the surface immediately below said excision resulting from the ablation defines a convex surface of the optically used area of the cornea.

31. A method for producing a surgical excision of controlled depth and shape in a cornea by ablative photochemical decomposition of corneal tissue without thermal damage to the corneal tissue, said method comprising the steps of:

(a) generating a laser beam in the far ultraviolet region of the energy spectrum and at a wavelength selected to produce ablative photochemical decomposition of corneal tissue without thermal damage to the corneal tissue;

(b) directing said radiation in a controlled manner onto said corneal tissue to induce ablative photochemical decomposition thereof in a volumetric removal of said corneal tissue without thermal heating to create a surgical excision of controlled depth and shape with depth penetration into the stroma; and (c) wherein the ablation overlaps the optically used area of the cornea and the surface immediately below said excision of controlled depth and shape resulting from the ablation defines a convex surface.

32. The method of claim 31 wherein said selected wavelength is 193 nanometers.

33. A method for producing a surgical excision of controlled depth and shape in a cornea by ablative photochemical decomposition of corneal tissue without thermal damage to the corneal tissue, said method comprising the steps of:

(a) generating a laser beam at a wavelength of 193 nanometer;

(b) directing said laser beam at a wavelength of 193 nanometers:

(c) controlling said laser beam so as to induce ablative photochemical decomposition of said corneal tissue in a volumetric removal of said corneal tissue without thermal damage to said corneal tissue to create a surgical excision of controlled depth and shape with depth penetration into the stroma; and (d) wherein the ablation overlaps the optically used area of the cornea and the surface immediately below said excision of controlled depth and shape resulting from the ablation defines a convex surface.

34. The method of changing optical properties of an eye by operating solely upon the anterior surface of the cornea of the eye, which method comprises selective ultraviolet irradiation and attendant ablative photo decomposition of the anterior surface of the cornea in a volumetric removal of corneal tissue and with depth penetration into the stroma and to a predetermined curvature profile, and wherein the ablation overlaps the optically used area of the cornea and the surface immediately below said volumetric removal of corneal tissue resulting from the ablation defines a convex surface.

35. The method of using an ultraviolet laser to change the optical properties of an eye, which method comprises the steps of:

adjusting the intensity of laser beam projection to a level at which laser beam projection onto the anterior surface of the cornea of the eye will result in corneal-tissue ablation per unit time which is but a fraction of a predetermined maximum ablation depth into the stroma of the cornea;

directing the laser beam at the anterior surface of the cornea in a controlled manner to create at least one excision in the anterior surface of the cornea relative to the optic axis thereof by volumetric removal of corneal tissue in the course of ablative photo decomposition of the stroma causing a redefinition of the anterior surface of the cornea; and wherein the ablation overlaps the optically used area of the cornea and the surface immediately below said excision resulting from the ablation defines a convex surface.

36. A method for producing a surgical excision of controlled depth and shape in a cornea by ablative photochemical decomposition of corneal tissue without thermal damage to the corneal tissue, said method comprising the steps of:

(a) generating a laser beam in the far ultraviolet region of the energy spectrum and at a wavelength selected to produce ablative photochemical decomposition of corneal tissue without thermal damage to the corneal tissue;

(b) directing said radiation in a controlled manner onto said corneal tissue to induce ablative photochemical decomposition thereof in a volumetric removal of said corneal tissue without thermal heating to create a surgical excision of controlled depth and shape with depth penetration into the stroma; and (c) wherein said step of generating comprises generating said radiation in pulses, and one of said pulses impinges on the optically used portion of the cornea in an area having a diameter of at least one hundred microns.

37. The method of claim 36 wherein said selected wavelength is 193 nanometers.

38. A method for producing a surgical excision of controlled depth and shape in a cornea by ablative photochemical decomposition of corneal tissue without thermal damage to the corneal tissue, said method comprising the steps of:

(a) generating a laser beam at a wavelength of 193 nanometers;

(b) directing said laser beam onto a predetermined area of corneal tissue;

(c) controlling said laser beam so as to induce ablative photochemical decomposition of said corneal tissue in a volumetric removal of said corneal tissue without thermal damage to said corneal tissue to create a surgical excision of controlled depth and shape with depth penetration into the stroma; and (d) wherein said step of generating comprises generating said laser beam in pulses, and one of said pulses impinges on the optically used portion of the cornea in an area having a diameter of at least one hundred microns.

39. The method of changing optical properties of an eye by operating solely upon the anterior surface of the cornea of the eye, which method comprises selective ultraviolet irradiation and attendant ablative photo decomposition of the anterior surface of the cornea in a volumetric removal of corneal tissue and with depth penetration into the stroma and to a predetermined curvature profile, and wherein said step of irradiation comprises generating pulses of radiation, and one of said pulses impinges on the optically used portion of the cornea in an area having a diameter of at least one hundred microns.

40. The method of using an ultraviolet laser to change the optical properties of an eye, which method comprises the steps of:

adjusting the intensity of laser beam projection to a level at which laser beam projection onto the anterior surface of the cornea of the eye will result in corneal-tissue ablation per unit time which is but a fraction of a predetermined maximum ablation depth into the stroma of the cornea;

directing the laser beam at the anterior surface of the cornea in a controlled manner to create at least one excision in the anterior surface of the cornea relative to the optic axis thereof by volumetric removal of corneal tissue in the course of ablative photo decomposition of the stroma causing a redefinition of the anterior surface of the cornea; and wherein said step of adjusting comprises generating said laser beam in pulses, and one of said pulses impinges on the optically used portion of the cornea in an area having a diameter of at least one hundred microns.

41. A method for producing a surgical excision of controlled depth and shape in a cornea by ablative photochemical decomposition of corneal tissue without thermal damage to the corneal tissue, said method comprising the steps of:

(a) generating a laser beam in the far ultraviolet region of the energy spectrum and at a wavelength selected to produce ablative photochemical decomposition of corneal tissue without thermal damage to the corneal tissue;

(b) directing said radiation in a controlled manner onto said corneal tissue to induce ablative photochemical decomposition thereof in a volumetric removal of said corneal tissue without thermal heating to create a surgical excision of controlled depth and shape with depth penetration into the stroma; and (c) wherein said step of generating comprises generating said laser beam in pulses, and one of said pulses has a diameter of at least one hundred microns at the cornea and overlaps the optically used area of the cornea.

42. The method of claim 41 wherein said selected wavelength is 193 nanometers.

43. A method for producing a surgical excision of controlled depth and shape in a cornea by ablative photochemical decomposition of corneal tissue without thermal damage to the corneal tissue, said method comprising the steps of:

(a) generating a laser beam at a wavelength of 193 nanometers;

(b) directing said laser beam onto a predetermined area of corneal tissue;

(c) controlling said laser beam so as to induce ablative photochemical decomposition of said corneal tissue in a volumetric removal of said corneal tissue without thermal damage to said corneal tissue to create a surgical excision of controlled depth and shape with depth penetration into the stroma; and (d) wherein said step of generating comprises generating said laser beam in pulses, and one of said pulses has a diameter of at least one hundred microns at the cornea and overlaps the optically used area of the cornea.

44. The method of changing optical properties of an eye by operating solely upon the anterior surface of the cornea of the eye, which method comprises selective ultraviolet irradiation and attendant ablative photo decomposition of the anterior surface of the cornea in a volumetric removal of corneal tissue and with depth penetration into the stroma and to a predetermined curvature profile, and wherein said step of irradiation comprises generating said irradiation in pulses, and one of said pulses has a diameter of at least one hundred microns at the cornea and overlaps the optically used area of the cornea.

45. The method of using an ultraviolet laser to change the optical properties of an eye, which method comprises the steps of:

adjusting the intensity of laser beam projection to a level at which laser beam projection onto the anterior surface of the cornea of the eye will result in corneal-tissue ablation per unit time which is but a fraction of a predetermined maximum ablation depth into the stroma of the cornea:

directing the laser beam at the anterior surface of the cornea in a controlled manner to create at least one excision in the anterior surface of the cornea relative to the optic axis thereof by volumetric removal of corneal tissue in the course of ablative photo decomposition of the stroma causing a redefinition of the anterior surface of the cornea; and wherein said step of adjusting comprises generating said laser beam in pulses, and one of said pulses has a diameter of at least one hundred microns at the cornea and overlaps the optically used area of the cornea.

46. A method for producing a surgical excision of controlled depth and shape in a cornea by ablative photochemical decomposition of corneal tissue without thermal damage to the corneal tissue, said method comprising the steps of:

(a) generating a laser beam in the far ultraviolet region of the energy spectrum and at a wavelength selected to produce ablative photochemical decomposition of corneal tissue without thermal damage to the corneal tissue;

(b) directing said radiation in a controlled manner onto said corneal tissue to induce ablative photochemical decomposition thereof in a volumetric removal of said corneal tissue without thermal heating to create a surgical excision of controlled depth and shape with depth penetration into the stroma; and (c) wherein said step of generating comprises generating said radiation in pulses, one of said pulses has a first diameter at the cornea, and a second one of said pulses has a second diameter at the cornea which is different from said first diameter.

47. The method of claim 46 wherein said selected wavelength is 193 nanometers.

48. A method for producing a surgical excision of controlled depth and shape in a cornea by ablative photochemical decomposition of corneal tissue without thermal damage to the corneal tissue, said method comprising the steps of:

(a) generating a laser beam at a wavelength of 193 nanometers;

(b) directing said laser beam onto a predetermined area of corneal tissue;

(c) controlling said laser beam so as to induce ablative photochemical decomposition of said corneal tissue in a volumetric removal of said corneal tissue without thermal damage to said corneal tissue to create a surgical excision of controlled depth and shape with depth penetration into the stroma; and (d) wherein said step of generating comprises generating said laser beam in pulses, one of said pulses has a first diameter at the cornea, and a second one of said pulses has a second diameter at the cornea which is different from said first diameter.

49. The method of changing optical properties of an eye by operating solely upon the anterior surface of the cornea of the eye, which method comprises selective ultraviolet irradiation and attendant ablative photo decomposition of the anterior surface of the cornea in a volumetric removal of corneal tissue and with depth penetration into the stroma and to a predetermined curvature profile, and wherein said step of irradiation comprises generating said irradiation in pulses, one of said pulses has a first diameter at the cornea, and a second one of said pulses has a second diameter at the cornea that is different from said diameter.

50. The method of using an ultraviolet laser to change the optical properties of an eye, which method comprises the steps of:

adjusting the intensity of laser beam projection to a level at which laser beam projection onto the anterior surface of the cornea of the eye will result in corneal-tissue ablation per unit time which is but a fraction of a predetermined maximum ablation depth into the stroma of the cornea;

directing the laser beam at the anterior surface of the cornea in a controlled manner to create at least one excision in the anterior surface of the cornea relative to the optic axis thereof by volumetric removal of corneal tissue in the course of ablative photo decomposition of the stroma causing a redefinition of the anterior surface of the cornea; and wherein said step of adjusting comprises generating said laser beam in pulses, one of said pulses has a first diameter at the cornea, and a second one of said pulses has a second diameter at the cornea that is different from said first diameter.

51. A method for producing a surgical excision of controlled depth and shape in a cornea by ablative photochemical decomposition of corneal tissue without thermal damage to the corneal tissue, said method comprising the steps of:

(a) generating a laser beam in the far ultraviolet region of the energy spectrum and at a wavelength selected to produce ablative photochemical decomposition of corneal tissue without thermal damage to the corneal tissue;

(b) directing said radiation in a controlled manner onto said corneal tissue to induce ablative photochemical decomposition thereof in a volumetric removal of said corneal tissue without thermal heating to create a surgical excision of controlled depth and shape with depth penetration into the stroma; and (c) wherein said step of generating comprises generating said laser beam in pulses, one of said pulses has a first dimension at the cornea, and a second one of said pulses has a second dimension at the cornea that is different from said dimension.

52. The method of claim 51 wherein said selected wavelength is 193 nanometers.

53. A method for producing a surgical excision of controlled depth and shape in a cornea by ablative photochemical decomposition of corneal tissue without thermal damage to the corneal tissue, said method comprising the steps of:

(a) generating a laser beam at a wavelength of 193 nanometers;

(b) directing said laser beam onto a predetermined area of corneal tissue;

(c) controlling said laser beam so as to induce ablative photochemical decomposition of said corneal tissue in a volumetric removal of said corneal tissue without thermal damage to said corneal tissue to create a surgical excision of controlled depth and shape with depth penetration into the stroma; and (d) wherein said step of generating comprises generating said laser beam in pulses, one of said pulses has a first dimension at the cornea, and a second one of said pulses has a second dimension at the cornea that is different from said first dimension.

54. The method of changing optical properties of an eye by operating solely upon the anterior surface of the cornea of the eye, which method comprises selective ultraviolet irradiation and attendant ablative photo decomposition of the anterior surface of the cornea in a volumetric removal of corneal tissue and with depth penetration into the stroma and to a predetermined curvature profile, and wherein said step of irradiation comprises generating radiation in pulses, one of said pulses has a first dimension at the cornea, and a second one of said pulses has a second dimension at the cornea that is different from said first dimension.

55. The method of using an ultraviolet laser to change the optical properties of an eye, which method comprises the steps of:

adjusting the intensity of laser beam projection to a level at which laser beam projection onto the anterior surface of the cornea of the eye will result in corneal-tissue ablation per unit time which is but a fraction of a predetermined maximum ablation depth into the stroma of the cornea;

directing the laser beam at the anterior surface of the cornea in a controlled manner to create at least one excision in the anterior surface of the cornea relative to the optic axis thereof by volumetric removal of corneal tissue in the course of ablative photo decomposition of the stroma causing a redefinition of the anterior surface of the cornea; and wherein said step of adjusting comprises generating said laser beam in pulses, one of said pulses has a first dimension at the cornea, and a second one of said pulses has a second dimension at the cornea that is different from said first dimension.

56. A method for producing a surgical excision of controlled depth and shape in a cornea by ablative photochemical decomposition of corneal tissue without thermal damage to the corneal tissue, said method comprising the steps of:
   (a) generating a laser beam in the far ultraviolet region of the energy spectrum and at a wavelength selected to produce ablative photochemical decomposition of corneal tissue without thermal damage to the corneal tissue;
   (b) directing said radiation in a controlled manner onto said corneal tissue to induce ablative photochemical decomposition thereof in a volumetric removal of said corneal tissue without thermal heating to create a surgical excision of controlled depth and shape with depth penetration into the stroma; and
   (c) wherein said ablative photochemical decomposition extends over an ablation area of the cornea, and that ablation area includes an area having a dimension of 750 microns in each of two perpendicular directions.

57. The method of claim 56 wherein said selected wavelength is 193 nanometers.

58. A method for producing a surgical excision of controlled depth and shape in a cornea by ablative photochemical decomposition of corneal tissue without thermal damage to the corneal tissue, said method comprising the steps of:
   (a) generating a laser beam at a wavlength of 193 nanometers;
   (b) directing said laser beam onto a predetermined area of corneal tissue;
   (c) controlling said laser beam so as to induce ablative photochemical decomposition of said corneal tissue in a volumetric removal of said corneal tissue without thermal damage to said corneal tissue to create a surgical excision of controlled depth and shape with depth penetration into the stroma; and
   (d) wherein said ablative photochemical decomposition extends over an ablation area of the cornea, and that ablation area includes an area having a dimension of 750 microns in each of two perpendicular directions.

59. The method of changing optical properties of an eye by operating solely upon the anterior surface of the cornea of the eye, which method comprises selective ultraviolet irradiation and attendant ablative photo decomposition of the anterior surface of the cornea in a volumetric removal of corneal tissue and with depth penetration into the stroma and to a predetermined curvature profile, and wherein said ablative photo decomposition extends over an ablation area of the cornea, and that ablation area includes an area having a dimension of 750 microns in each of two perpendicular directions.

60. The method of using an ultraviolet laser to change the optical properties of an eye, which method comprises the steps of:

adjusting the intensity of laser beam projection to a level at which laser beam projection onto the anterior surface of the cornea of the eye will result in corneal-tissue ablation per unit time which is but a fraction of a predetermined maximum ablation depth into the stroma of the cornea;

directing the laser beam at the anterior surface of the cornea in a controlled manner to create at least one excision in the anterior surface of the cornea relative to the optic axis thereof by volumetric removal of corneal tissue in the course of ablative photo decomposition of the stroma causing a redefinition of the anterior surface of the cornea; and wherein said ablative photo decomposition of said stroma extends over an ablation area of said stroma, and that ablation area includes an area having a dimension of 750 microns in each of two perpendicular directions.

61. A method for producing a surgical excision of controlled depth and shape in a cornea by ablative photochemical decomposition of corneal tissue without thermal damage to the corneal tissue, said method comprising the steps of:
   (a) generating a laser beam in the far ultraviolet region of the energy spectrum and at a wavelength selected to produce ablative photochemical decomposition of corneal tissue without thermal damage to the corneal tissue;
   (b) directing said radiation in a controlled manner onto said corneal tisse to induce ablative photochemical decomposition thereof in a volumetric removal of said corneal tissue without thermal heating to create a surgical excision of controlled depth and shape with depth penetration into the stroma; and
   (c) wherein said penetration into the stroma is a partial penetration through the stroma in the optically used area of the cornea.

62. The method of claim 61 wherein said selected wavelength is 193 nanometers.

63. A method for producing a surgical excision of controlled depth and shape in a cornea ablative photochemical decomposition of corneal tissue without thermal damage to the corneal tissue, said method comprising the steps of:
   (a) generating a laser beam at a wavelength of 193 nanometers;
   (b) directing said laser beam onto a predetermined area of corneal tissue;
   (c) controlling said laser beam so as to induce ablative photochemical decomposition of said corneal tissue in a volumetric removal of said corneal tissue without thermal damage to said corneal tissue to create a surgical excision of controlled depth and shape with depth penetration into the stroma; and
   (d) wherein said penetration into the stroma is a partial penetration through the stroma in the optically used area of the cornea.

64. The method of changing optical properties of an eye by operating solely upon the anterior surface of the cornea of the eye, which method comprises selective ultraviolet irradiation and attendant ablative photo decomposition of the anterior surface of the cornea in a volumetric removal of corneal tissue and with depth penetration into the stroma and to a predetermined curvature profile, wherein said penetration into the stroma is a partial penetration through the stroma in the optically used area of the cornea.

65. The method of using an ultraviolet laser to change the optical properties of an eye, which method comprises the steps of:

adjusting the intensity of laser beam projection to a level at which laser beam projection onto the anterior surface of the cornea of the eye will result in corneal-tissue ablation per unit time which is but a fraction of a predetermined maximum ablation depth into the stroma of the cornea;

directing the laser beam at the anterior surface of the cornea in a controlled manner to create at least one excision in the anterior surface of the cornea relative to the optic axis thereof by volumetric removal of corneal tissue in the course of ablative photo decomposition of the stroma causing a redefinition of the anterior surface of the cornea; and wherein said photo ablation of the stroma is a partial penetration through the stroma in the optically used area of the cornea.

* * * * *